(12) United States Patent
Joshi et al.

(10) Patent No.: US 9,192,625 B1
(45) Date of Patent: Nov. 24, 2015

(54) ANTIMICROBIAL NANOCOMPOSITE COMPOSITIONS, FIBERS AND FILMS

(76) Inventors: Mangala Joshi, New Delhi (IN); Roli Purwar, Haryana (IN); Jayant Subhash Udakhe, Yavatmal (IN); Rajagopalan Sreedevi, Bangalore (IN)

( * ) Notice: Subject to any disclaimer, the term of this patent is extended or adjusted under 35 U.S.C. 154(b) by 0 days.

(21) Appl. No.: 13/175,616

(22) Filed: Jul. 1, 2011

(51) Int. Cl.
*A61K 33/06* (2006.01)
*D04H 1/00* (2006.01)

(52) U.S. Cl.
CPC *A61K 33/06* (2013.01); *D04H 1/00* (2013.01); *C08L 2203/00* (2013.01)

(58) Field of Classification Search
None
See application file for complete search history.

(56) References Cited

U.S. PATENT DOCUMENTS

| | | | |
|---|---|---|---|
| 6,266,951 B1 * | 7/2001 | Chakravarti | 57/210 |
| 6,358,576 B1 * | 3/2002 | Adur et al. | 428/34.2 |
| 7,385,101 B2 | 6/2008 | Chandra et al. | |
| 7,462,753 B2 | 12/2008 | Ma et al. | |
| 7,592,387 B2 | 9/2009 | Kim et al. | |
| 7,666,476 B2 | 2/2010 | Chandra et al. | |
| 2002/0064653 A1 * | 5/2002 | Ladika et al. | 428/364 |
| 2004/0173056 A1 | 9/2004 | McNally et al. | |
| 2004/0191522 A1 * | 9/2004 | Haring et al. | 428/411.1 |
| 2004/0266546 A1 * | 12/2004 | Huang | 473/300 |
| 2005/0199094 A1 | 9/2005 | Chandra et al. | |
| 2006/0067965 A1 | 3/2006 | Chandra et al. | |
| 2006/0202177 A1 * | 9/2006 | Chen | 252/609 |
| 2009/0074826 A1 | 3/2009 | Naik | |
| 2009/0123723 A1 * | 5/2009 | Kliesch et al. | 428/220 |
| 2009/0247973 A1 | 10/2009 | Yeh et al. | |
| 2010/0063434 A1 | 3/2010 | Naik | |
| 2011/0142899 A1 * | 6/2011 | Lagaron Abello et al. | 424/405 |

FOREIGN PATENT DOCUMENTS

| | | |
|---|---|---|
| GB | 2450475 A | 12/2008 |
| WO | 2008024426 A2 | 2/2008 |
| WO | WO 2008152417 A2 * | 12/2008 |
| WO | WO 2009156975 A1 * | 12/2009 |

OTHER PUBLICATIONS de Azeredo, Henriette, Nanocomposites for food packaging applications, Mar. 30, 2009, Food Research International, vol. 42, pp. 1240-1253.*
Sigma-Aldrich Co., Nanoclays for Composites, Oct. 2008, Sigma-Aldrich Chemistry Website (found by Way back machine).*
Mani et al (Size Reduction of Clay Particles in Nanometer Dimensions, 2003, Materials Research Society Symposium Proclamation, vol. 740, pp. 113-118).*
Smart et al. (IMRI: Journal Articles, paper 66, 2008, pp. 1-36).*
Magana et al (Journal of Molecular Catalysis A: Chemical, 2008, vol. 281, pp. 192-199).*
Dolgovskij et al (ANTEC, 2003, pp. 2255-2259).*
Alexandre, et al.; "Polymer-layered silicate nanocomposites: preparation, properties and uses of a new class of materials"; Materials Science and Engineering: R: Reports, vol. 28, Issues 1-2, Jun. 15, 2000, pp. 1-63.
Nigmatullin, Rinat et al.; "Polymer-layered silicate nanocomposites in the design of antimicrobial materials"; Journal of Materials Science; vol. 43, No. 17, (2008) pp. 5728-5733.
Zhou, Yuhang et al.; "Antimicrobial ability of Cu2+-montmorillonite"; Applied Clay Science, vol. 27, Issues 3-4, Dec. 2004, pp. 215-218.
Hu, Cai-Hong et al.; "Adsorption and antibacterial effect of copper-exchanged montmorillonite on Escherichia coli K88", Applied Clay Science, vol. 31, Issues 3-4, Mar. 2006, pp. 180-184.
Magana, S.M. et al.; "Antibacterial activity of montmorillonites modified with silver", Journal of Molecular Catalysis A: Chemical, vol. 281, Issues 1-2, Feb. 18, 2008, pp. 192-199.
Malachova, Katerina et al.; "Antibacterial and antifungal activities of silver, copper and zinc montmorillonites"; Applied Clay Science, vol. 53, Issue 4, Oct. 2011, pp. 642-645.
Aihara, Nariaki et al.; "Preparation and Characterization of Gold and Silver Nanoparticles in Layered Laponite Suspensions"; Langmuir, 1998, 14 (17), pp. 4945-4949.
Zhao, Difang et al.; "Preparation and characterization of Mingguang palygorskite supported with silver and copper for antibacterial behavior"; Applied Clay Science, vol. 33, Issues 3-4, Aug. 2006, pp. 161-170.
Top, Ayben et al.; "Silver, zinc, and copper exchange in a Na-clinoptilolite and resulting effect on antibacterial activity"; Applied Clay Science, vol. 27, Issues 1-2, Oct. 2004, pp. 13-19.
Meng, Na et al.; "Controlled release and antibacterial activity chlorhexidine acetate (CA) intercalated in montmorillonite"; International Journal of Pharmaceutics, vol. 382, Issues 1-2, Dec. 1, 2009, pp. 45-49.
Wang, Xiaoying et al.; "Preparation, characterization and antimicrobial activity of chitosan/layered silicate nanocomposites"; Polymer, vol. 47, Issue 19, Sep. 7, 2006, pp. 6738-6744.
Rhim, Jong-Whan et al.; "Tensile, water vapor barrier and antimicrobial properties of PLA/nanoclay composite films, LWT"; Food Science and Technology, vol. 42, Issue 2, Mar. 2009, pp. 612-617.

(Continued)

*Primary Examiner* — Brian-Yong Kwon
*Assistant Examiner* — Mark V Stevens
(74) *Attorney, Agent, or Firm* — Howard IP Law Group, PC

(57) ABSTRACT

In the present disclosure, silver ions, copper ions, quaternary ammonium compounds and cationic drugs such as sulphanilamide, chlorhexidine acetate, etc., used as antibacterial agents are incorporated into fibers, filaments and films through nanoclays. The nanoclays serve as a carrier for the antimicrobial agents and are incorporated into the fiber-forming polymer. In one embodiment, the biocidal metals and organic compounds are incorporated into the clay structure via an ion exchange reaction. Nylon nanocomposite filaments and films based on copper and quaternary ammonium ion modified clays provide 100% antibacterial activity against Gram positive *Staphylococcus aureus* and Gram negative *Escherichia coli* bacteria at an optimum clay loading of 0.75% (by weight), and the activity is retained up to 50 washes. The resulting filaments show enhanced mechanical properties such as tensile strength and modulus, and find application in areas of medical textiles like sutures, wound dressings and health & hygiene textiles. In addition, they can be integrated into protective clothing, body garments, sportswear and upholstery.

16 Claims, 13 Drawing Sheets

(56) References Cited

OTHER PUBLICATIONS

Nakashima, Harunobu et al.; "Elution of Metals with Artificial Sweat/Saliva from Inorganic Antimicrobials/Processed Cloths and Evaluation of Antimicrobial Activity of Cloths", J. Health Sci., vol. 54, (2008) pp. 390-399.

Praus, Petr et al.; "Study of Silver Adsorption on Montmorillonite"; J. Braz. Chem. Soc., vol. 19, No. 3, 2008, pp. 549-556.

Su, Hong-Lin et al.; "The disruption of bacterial membrane integrity through ROS generation induced by nanohybrids of silver and clay"; Biomaterials, vol. 30, Issue 30, Oct. 2009, pp. 5979-5987.

Tong, Guo et al., "Antibacterial effects of the Cu(II)-exchanged montmorillonite on Escherichia coli K88 and Salmonella choleraesuis", Veterinary Microbiology, vol. 105, Issue 2, Jan. 31, 2005, pp. 113-122.

Biello, David; "How Do You Stop Flesh-Eating Bacteria? Apply Some Clay"; Scientific American; Nov. 9, 2007.

Melville, Kate; "Clays Exhibit Novel Antibacterial Properties"; www.scienceagogo.com/news/20061001221856data_trunc_sys.shtml; Nov. 2, 2006.

Hu, C.H. et al.; "Antibacterial effect of Cu2+-exchanged montmorillonite on Aeromonas hydrophila and discussion on its mechanism", Veterinary Microbiology, vol. 109, Issues 1-2, Aug. 10, 2005, pp. 83-88.

\* cited by examiner

ANTIMICROBIAL NANOCOMPOSITE COMPOSITIONS, FIBERS AND FILMS

FIELD OF THE DISCLOSURE

The invention generally relates to the field of antimicrobial materials, and more particularly to antimicrobial nanocomposite fibers and films for use in health & hygiene as well as medical textile applications.

BACKGROUND OF THE DISCLOSURE

Textiles provide an excellent medium for the growth of microorganisms when the basic requirements such as nutrients, moisture, oxygen, and appropriate temperature are present. The large surface area of textiles also assists in the growth of microorganisms on the fabric. The major problems associated with microorganism growth in textiles are related to hygiene and fabric deterioration. With existing technologies, antimicrobial compounds such as silver, copper, quaternary ammonium compounds are generally applied on the fibers either through coating or are added during melt mixing prior to spinning. The major drawbacks of these fibers are that the antimicrobial compounds release very fast. The amount of antimicrobial agent released during laundering is also high, which affects the durability of the finished fabric. Metals such as silver are generally applied on the fibers in the form of a very thin coating deposited through a sputtering technique, an example of which is the commercial antimicrobial nylon fibre "X-STATIC®". This thin film coating is prone to crack during processing and use due to the mismatch in extensibility between the fibre and the coating. Apart from this, the strength of the fibre/fabric is also often reduced after the application of a durable antimicrobial coating or finishing.

Thus, there remains a need for a highly durable anti-microbial textile material having enhanced retention of antimicrobial properties upon repeated use and washings without affecting the textile properties such as handle and feel. The controlled release of active agent over a period of time is also a desirable property for certain applications.

The modification of nanoclays with organic compounds and their application as nano-filler finds use in the preparation of hybrid polymer nanocomposite materials due to improved mechanical, thermal, electrical, barrier and optical properties. See Alexandre, M., Dubois, P., Materials Science and Engineering. 28, 2000, pp. 1-63. Organic modified clay is generally prepared through ion exchange of the metal cations in the clay with organophilic cations such as quaternary ammonium salts. It has been reported recently that organoclay containing cationic surfactant or quaternary ammonium salt and long hydrophobic chain show excellent antimicrobial properties. See Nigmatullin, R., Gao, F., Konovalova, V., Journal of Material Science. 43, 2008, 5728. The use of clays such as Montmorillonite, Laopnite, Mingguang Polygorskite, AND Na-clinoptilolite as a support medium or carrier for antimicrobial agents as well as antimicrobial drug has also been reported recently due to their potential use in water treatment, food packaging, and drug delivery material. See Zhou, Y., Xia, M., Ye, Y., Applied Clay Science, 27 (2004) 215; Hu, C-H., Xia, M-S. Applied Clay Science. 31 (2006)180; Magana, S. M., Quintana, P., Aguilar, D. H., Toledo, J. A., Angeles-Chavez, C., Cortes, M. A., Leon, L., Freile-Pelegrm, Y., Lopez, T., Torres Sanchez e, R. M., Journal of Molecular Catalysis A: Chemical. 281 (2008)192; Malachová, K., Praus, P., Pavlíčková, Z., Turicová, M., Applied Clay Science. 43 (2009) 364; Aihara, N., Torigoe, K., Esumi, K., Langmuir. 14 (1998) 4945; Zhao, D., Zhou, J., Liu, N., Applied Clay Science 33 (2006) 161; and Top, A., Ülkú, S. Applied Clay Science, 27 (2004).

The antimicrobial agents such as silver, copper, quaternary ammonium compounds, cationic drugs and like have been intercalated and absorbed on clay surfaces through an ion exchange mechanism. These incorporated antimicrobial/active ions/drugs subsequently release from the clay surface in a controlled manner and show excellent antimicrobial activity against pathogenic bacteria.

Montmorillonite (MMT) is classified as 2:1 phyllosilicate clay. It has a unit crystal lattice formed by one alumina octahedral sheet sandwiched between two silica tetrahedral sheets and the interlayer between units contain positive cations such as $Na^+$, $K^+$, $Ca^{++}$ etc. and water molecules. Due to this crystalline arrangement, montmorillonite is able to expand and contract the interlayer while maintaining two dimensional crystallographic integrity and is characterized by octahedral and/or tetrahedral substitution and high ion exchange capacities (70-120 mequiv/100 g). Magana et al., have studied the antimicrobial activity of the montmorillonite clay modified with silver and found that the antimicrobial activity or silver loading on the clay is dependent on the cation exchange capacity of the clay and the availability of ionic silver to be in contact with the bacteria. The cation exchange capacity of the clay can be modified via thermal, mechanical or chemical treatments. See Top et al. Hu and Xia have studied three different kinds of montmorillonite such as calcium montmorillonite, sodium montmorillonite and acid activated montmorillonite and their ion exchange with $Cu^{++}$. See Hu et al. The $Cu^{++}$ modified clays shows very good antimicrobial activity. Menga et al., have studied chlorhexidine acetate (CA)/montmorillonite intercalation composites and its antimicrobial potential with pathogenic bacteria, *Staphylococcus aureus* and *Pseudomonas aeruginosa*. See Menga, Na., Zhoua, N.-L., Zhang, S-Q., Shena, J. International Journal of Pharmaceutics, 382 (2009).

The application of quaternary ammonium ion based antimicrobial clay into a polymer matrix in the form of films has been explored recently. The introduction of commercially available organo-clays such as Closite 30B and Closite 10A into Nylon 6, Chitosan and PLA matrix significantly suppresses biofilm formation on film surfaces exposed to the bacterial suspension. See Nigmatullin et al.; Wang, X., Du,Y., Yang, J., Wang, X., Shi, X., Hu, Y., Polymer, 47 (2006) 6738; and Rhim, J. W., Hong, S. I., Ha, C. S., LWT Food Science and Technology, 42 (2009) 612. However, there is no literature available on the application of antimicrobial clay based on metal ions in polymer nanocomposite and more specifically for making antimicrobial fibers.

SUMMARY OF THE DISCLOSURE

In the present disclosure, antimicrobial clay has been prepared using silver, copper and sulphanilamide (cationic) drug through an ion exchange reaction. The process parameters such as temperature, time and chemical treatment of clay were varied to obtain maximum loading of $Ag^+$, $Cu^{++}$ ions and drug cation on the montmorillonite. The antimicrobial activity of the modified clays as well as the commercial Cloisite clay 30B which contains antimicrobial quaternary ammonium ion was assayed against Gram positive bacteria *Staphylococcus aureus* and Gram negative bacteria *Escherichia coli*.

Further, in the present disclosure, the silver, copper, quaternary ammonium compounds and cationic drug based antimicrobial agents are incorporated into the fibers through nanoclays. These modified nanoclays are termed as antimicrobial clays. The nanoclays here serve as a carrier for the antimicrobial agents and are incorporated into the fibre-forming polymer. During use, the antimicrobial compounds release from the fibre matrix in a controlled manner and provide excellent antimicrobial activity against skin flora. The incorporation of antimicrobial agents through nanoclays does not affect the mechanical properties like tensile strength of the fibers. Rather, in most cases the tensile strength of the fibers increases due to the addition of the nanoclay.

Thus, in the present disclosure antimicrobial fibers are produced by incorporating modified nanoclays which have antimicrobial properties. The clay minerals are used as a carrier for antimicrobial metals such as silver, copper, quaternary ammonium ions, cationic drugs etc. In one embodiment, the antimicrobial metals and organic compounds are incorporated into the clay structure via an ion exchange reaction. Nanoparticles of neutral metals are formed inside the clay gallery by the reduction of metal salts loaded into the clay. These silver nanoparticles are formed as a result of combination of ion-exchange, surface adsorption and reduction process. Initially the cations such as $Na^+$, $K^+$, etc. present in the clay gets exchanged with the metal ion such as $Ag^+$ during the ion-exchange process. Some of the $Ag^+$ ions are also adsorbed on the surfaces of the clay platelets which are negatively charged and thus attract the positively charged $Ag^+$ ions. During this time, chemical reduction process leads to formation of silver nanoparticles of very small size in the range of 5-15 nm. These nanoparticles are formed only in case of Ag-MMT and not in Cu-MMT, the reason being the difference in their chemical reduction potential.

Antimicrobial clays that incorporate antimicrobial metal, quaternary ammonium ions and cationic drugs in this manner provide effective antimicrobial activity against skin flora. The antimicrobial clays can be loaded on the fibers through a melt intercalation process to produce antimicrobial fibers.

The nylon nanocomposite fibre based on silver intercalated clays provides moderate antimicrobial activity (53%) while their nanocomposite films show 100% activity. The nylon nanocomposite fibers and films based on copper and quaternary ammonium ion modified clays provide 100% antimicrobial activity, as per American Association of Textile Chemists and Colorists (AATCC) Test Method 100, against Gram positive *Staphylococcus aureus* and Gram negative *Escherichia coli* bacteria at an optimum clay loading of 0.75 wt. %, and the activity is retained up to 50 washes. This is but one embodiment, and excellent antimicrobial activity is expected with clay loading of from 0.1% to about 10% by weight of the polymer/clay nanocomposite. A slow release of active agents on demand is another advantage of the disclosed method and materials. Further, the addition of modified clays also enhances the tensile strength (about 4-11%) and tensile modulus (about 12-20%) of the nanocomposite fibers over neat nylon fibers.

The present disclosure is based on use of antimicrobial nanoclays which are dispersed at the nano level in the polymer matrix and thus provide very effective antimicrobial activity at low clay loadings. The incorporation of the clay is through a melt extrusion process which is easy to scale up with the existing synthetic fiber manufacturing technology. These antimicrobial clays are thermally stable, and hence are easily dispersed in the polymer at the melt stage unlike the organic conventional antimicrobial agents which are thermally unstable and cannot be easily processed through a melt process.

Thus, nylon and polypropylene based nanocomposite fibers with antimicrobial and drug delivery property have been developed. Organic and inorganic cationic antimicrobial agents such as silver, copper, long chain quaternary ammonium compounds and antimicrobial drugs which are cationic in nature such as chlorhexidene acetate and Sulphanilamide have been incorporated in the polymer matrix using montmorillonite nano clay as the carrier. These antimicrobial drugs are broadly for use in controlling infections caused by microbes.

As previously noted, the advantage of using the clay as a carrier material for antimicrobial agents is that the antimicrobial agent releases slowly from the polymer matrix on demand to effectively inhibit the growth of the bacteria. Another advantage is that the antimicrobial agents are evenly dispersed throughout the fibers as the clay gets exfoliated and intercalated into the polymer matrix at the nano level. Because these clays have superior thermal stability, the drugs and antimicrobial agents loaded into the clay can be easily incorporated into the polymer through a melt processing technique.

The fibers also show enhanced mechanical properties such as tensile strength and modulus, and can find application in areas of medical textiles like sutures, wound dressings and health & hygiene textiles. In addition, they can be integrated into protective clothing, body garments, sportswear and upholstery like carpets. The fibers are suitable for use in any of a variety of common textile manufacturing techniques, such as weaving, knitting, non-woven formations, and the like.

An antimicrobial composition is disclosed, comprising an antimicrobial agent, a nanoclay, and a polymer.

A method of making an antimicrobial composition is also disclosed, comprising incorporating a first quantity of an antimicrobial agent into a nanoclay to provide a loaded nanoclay composition, and incorporating a second quantity of the loaded nanoclay composition into a polymer.

An antimicrobial fiber is further disclosed, comprising an antimicrobial agent, a nanoclay, and a polymer.

A method of making an antimicrobial fiber is also disclosed, comprising incorporating a first quantity of an antimicrobial agent into a nanoclay to provide a loaded nanoclay composition, incorporating a second quantity of the loaded nanoclay composition into a polymer, and forming the resulting composition into a fiber.

BRIEF DESCRIPTION OF THE DRAWINGS

The details of the invention, both as to its structure and operation, may be obtained by a review of the accompanying drawings, in which like reference numerals refer to like parts, and in which.

DETAILED DESCRIPTION

Figure 1:
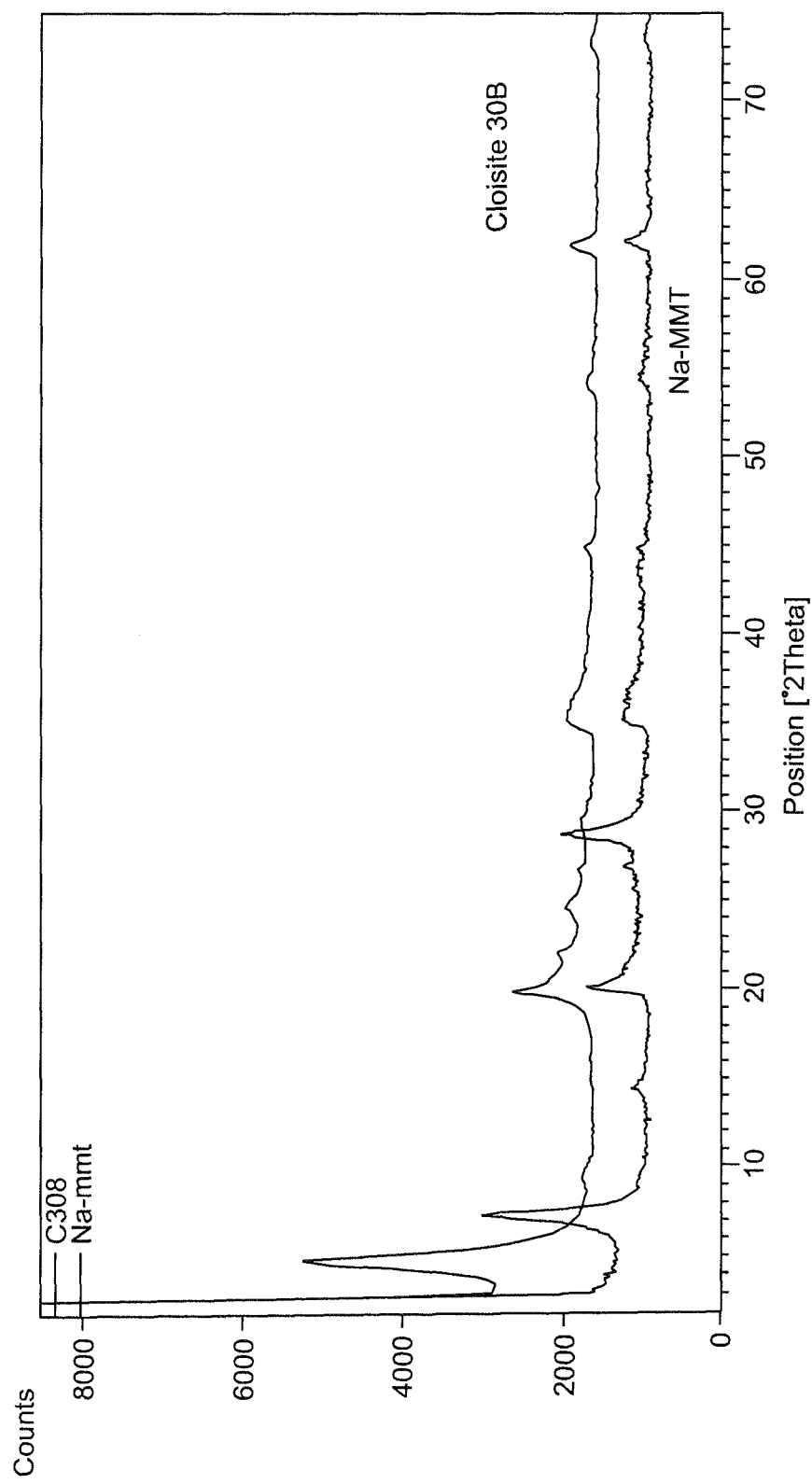
FIG. 1 illustrates the X-ray diffractrogram of Sodium montmorillonite and Cloisite 30B.

In the present disclosure, modified MMT clay has been prepared using silver, copper salts and Sulphanilamide drug with an aim to achieve higher loadings of $Ag^+$, $Cu^{++}$ and Sulphanilamide drug cations in the clay through an ion exchange reaction. The process parameters such as temperature, time and chemical treatment of clay were varied to obtain maximum loading of $Ag^+$, $Cu^{++}$ and Sulphanilamide drug cations on the montmorillonite. The antimicrobial activity of the modified clays as well as the commercial Cloisite clay 30B was assayed against Gram positive bacteria *Staphylococcus aureus* and Gram negative bacteria *Escherichia coli*.

In the present disclosure, silver, copper and Sulphanilamide intercalated clay is used to prepare nylon 6/clay nanocomposite fibers and films for antimicrobial activity. The quaternary ammonium compound modified commercial clay Cloisite 30 B has also been used to prepare nylon 6/clay nanocomposite fibers and films. The structure and morphology of these fibers has been studied using techniques such as XRD, SEM and TEM. The antimicrobial activity and mechanical properties of the nanocomposite fibers and films are discussed in detail below.

Nylon nanocomposite fibers and films produced using these antimicrobial clays (e.g., Cu-MMT (copper modified montmorillonite) and $NH_4^+$-MMT (Cloisite 30B)) show 100% activity against Gram positive *Staphylococcus aureus* and Gram negative *Escherichia coli* bacteria at an antimicrobial clay loading ranging from about 0.1% to about 10% by weight of the polymer nanocomposite fibers. Fibers based on Ag-MMT (silver modified montmorillonite) show a moderate activity (about 50%) against the tested bacteria, while the films show 100% activity.

The antimicrobial activity of these films/fibers is durable, and is retained up to 50 wash cycles when washed in accordance with ISO 2. The nanocomposite films based on these antimicrobial clays also show very good antimicrobial activity. The nanocomposite fibers at an optimized antimicrobial clay loading of about 0.1% to about 3% (by weight of the polymer nanocomposite fibers) also show enhanced tensile strength and modulus with marginal decrease in elongation at break. The produced nanocomposite fibers, which as noted have durable bioactivity against wide spectrum of microbes, can be used in a wide variety of application in the area of medical textiles, sportswear, upholstery, under garments, and the like.

Materials

Nylon 6 Chips (melting temperature 224*C, Density 1.14 g/CC) were supplied by M/s SRF Limited, Chennai, India. Sodium Montmorillonite (Na-MMT) clay and Cloisite 30 B (quaternary ammonium salt modified montmorillonite) clay were procured from Kunimine Industries Co. Ltd. Japan and Southern Clay Products USA respectively. Reagent grade chemicals Silver Nitrate (Merck), Copper Chloride (Merck), Sulphanilamide drug (Loba Chemie), Acetone (Merck), Nutirent Broth (Hi Media), Agar Agar (Qualigen) and DI water were used for the experiments.

Methods for Preparing Antimicrobial Clay

Preparation of Silver Montmorillonite Clay

The silver montmorillonite clays were prepared through an ion exchange reaction between the cations such as $Na^+$ present within the clay, and the $Ag^+$ present in a silver nitrate solution. The Na-MMT clay was ball milled (at 200 rpm for 30 min) and sonicated (for 1 hour) before the ion exchange reaction. The final average particle size of the clay was 500 nm as determined from a Particle Size Analyzer (BECKMAN COULTER Delsa Nano C DLS). For the ion exchange reaction, the Na-MMT clay (12.5 grams (gm)) was dispersed in 1 Liter (L) of deionized (DI) water. The clay dispersion was continuously stirred at 500 revolutions per minute (rpm) for 90 minutes at 25° C. The silver nitrate solution (concentration 6.12 gm/L) was added slowly to the clay dispersion. The ion exchange reactions were carried out for different process conditions as shown in Table 1 below by varying the reaction time and temperature. After the ion exchange reaction the modified clays were washed three times with distilled water in a centrifuge (at 7000 rpm for 30 min), until the filtration was free of $Ag^+$ ions.

TABLE 1

Different Conditions for Ion Exchange Reaction

| S. N | Clay Code | Reaction Temperature ° C. | Reaction Time |
|---|---|---|---|
| 1 | Ag-MMT (60 C 6 h) | 60 | 6 hours |
| 2 | Ag-MMT (30 C 3 D) | 30 | 3 Days |
| 3 | Ag-MMT (30 C 7 D) | 30 | 7 Days |

Preparation of Copper Montmorillonite Clay

The ball milled (200 rpm, 30 min) and sonicated (1 h) Na-MMT clay with average particle size of 500 nm was used for the preparation of Cu-MMT clay. The Na-MMT clay (12.5 gm) was dispersed in 1 L of DI water. The clay dispersion was continuously stirred at 500 rpm for 90 min at 25° C. The copper chloride solution (concentration 8.524 gm/L) was added slowly to the clay dispersion. The ion exchange reactions were carried out at 60° C. for 6 hours and the modified clay is referred as Cu-MMT. After the ion exchange reaction the Cu-MMT clay was washed three times with distilled water in a centrifuge (7000 rpm for 30 min) and dried.

An alternate technique was also used to prepare the copper montmorillonite clay, in which the Na-MMT clay was first acid modified and then an ion exchange reaction was carried out. The Na-MMT clay (70 gm) was mixed with 0.05 mol HCl solution. The dispersion was maintained for 24 h at temperature 30° C. with continuous stirring. After the acid modification, the clay was washed with distilled water in a centrifuge machine (700 rpm, 30 min). The acid modified clay was then ion exchanged with copper chloride solution as described above. The modified clay was referred as Cu-AM-MMT.

Finally the modified clay was washed with distilled water in a centrifuge machine and dried. Based on metal ion exchange reaction conditions five different metal biocide clays were prepared.

Preparation of Sulphanilamide Modified Clay (SA-MMT)

The ball milled (200 rpm, 30 min) and sonicated (1 h) Na-MMT clay with average particle size of 500 nm was used for the preparation of SA-MMT clay. The Na-MMT clay (1 gm) was dispersed in 50 ml of DI water. The clay dispersion was continuously stirred at 500 rpm for 30 min at 25° C. The Sulphanilamide solution (concentration 0.013 gm/ml, pH 4.1 adjusted with $H_3PO_4$) was added slowly to the clay dispersion. The ion exchange reactions were carried out at 90° C. for 3 hours and the modified clay is referred as SA-MMT. After the ion exchange reaction the SA-MMT clay solution Centrifuged (7000 Rpm For 30 Min) And The Clay Was Dried.

Characterization of Clays

X-Ray Diffraction

The change of d-spacing for the modified clays was studied on wide angle X ray diffractometer (Philips) using a Ni-filtered CuKα radiation of 1.5418 Angstroms (Å).

Energy Dispersive X-Ray Spectroscopy (EDXS)

A ZEISS (Model: EVO 50) SEM equipped with EDXS attachment was used for the quantitative elemental composition determination of the modified clays. The pastes of different clays were made in isopropanol and mounted on an EDXS sample holder. The samples were stubbed and coated with carbon to prevent charging in the electron beam.

Transmission Electron Microscopy (TEM)

The morphological characteristics of the silver modified clays were examined using a high resolution (Phillips C M 12) TEM machine. 0.01% of clay solution was made in 20 milliliters (ml) isopropanol then the solution was sonicated for 30 minutes. A drop of dilute clay solution was placed on a 300 mesh TEM special grid using a syringe, and allowed to dry in air. The samples were viewed under TEM.

Particle Size Analysis

Particle size analysis was carried out on a BECKMAN COULTER Delsa Nano C particle size analyzer. Clay (0.1 wt %) was suspended in 20 ml DI water and sonicated for 5 min to form a stable dispersion. The clay suspension was kept for 1 h before analysis of particle size.

Inductive Coupled Plasma Spectroscopy (ICP)

Inductively coupled plasma-optical emission spectrometry (ICP-OES Perkin Elmer OPTIMA 3000) was used to measure the quantity of silver and copper concentration on modified clay samples. Clay samples (0.5 g) were incinerated in a digitally controlled furnace. Temperature was gradually increased to 600° C. and then maintained for 60 min. Remaining ashes were dissolved in concentrated nitric acid in a 50-ml volumetric flask, which was then filled with double-distilled water to the indication line. All solutions were stored in plastic containers at room temperatures unless otherwise noted. Measurements for each sample were performed in triplicate and average results are reported.

Evaluation of Antimicrobial Activity of Clay

Antimicrobial activity of clays was determined qualitatively by a disc diffusion method and minimum inhibitory concentration (MIC) was evaluated by a colony counting method.

Disc Diffusion Test

Antimicrobial activity of the modified clays and Cloisite 30B was tested against Gram positive bacteria *Staphylococcus aureus* and Gram negative bacteria *Escherichia coli* by a disc diffusion test. The bacteria strain was cultured on Luria broth solution at 37° C. for 24 h. The stock solution contained $2\text{-}8\times10^7$ Colony Forming Units/milliliter (cfu/ml). The 10 μl ($10^5$ cfu/ml) of inoculum was spread on a Luria agar plate. The modified clays (100 mg) were pasted on the disc evenly and exposed to UV radiation for 30 min to ensure sterilization. The sterilized discs were placed over the surface of the inoculated agar plates. The sodium chloride solution (20 μl 0.1% w/v) was added to the agar medium to act as counter ions for diffusion of $Ag^+/Cu^{++}$ ions. The zone of inhibition was measured after 24 h of incubation at 37° C.

Minimum Inhibitory Concentration (MIC)

Minimum inhibitory concentration (MIC) is defined as the lowest concentration of antimicrobial agent which inhibits a visible growth of bacteria colony. MIC of the modified clays and Cloisite 30B was determined by the colony counting method. Clays at different concentration levels ranging from 10,000 ppm to 10 ppm were dispersed in a conical flask containing 10 ml Luria broth solution, then inoculated with 10 μl of Bacteria strain ($10^7$ cfu/ml) suspension and kept for 24 h at 37° C. After incubation, serial dilution of the liquid was made in sterilized distilled water. Dilution of $10^{-4}$ and $10^{-5}$ were used for colony counting. 10 μl was spread onto the agar plate and plates were incubated at 37° C. for 24 h. After incubation bacterial colonies were counted.

$$\text{Antimicrobial activity (\%)} = (A-B)/A \times 100, \text{ where:}$$

A=No. of colonies in control sample

B=No. of colonies in treated samples

Preparation of Nylon and Nylon Clay Nanocomposite Fibers

Nylon and nylon clay nanocomposite fibers were prepared by using a melt intercalation method. Five different nylon/clay master batches, namely Nylon/Na-MMT, Nylon/Cloisite 30B, Nylon/Ag-MMT, Nylon/Cu-MMT and Nylon SA-MMT, were prepared by using 10% of antimicrobial clay by weight of the polymer/clay nanocomposite. The different clays were dispersed in acetone and ultrasonicated for 30 min. The nylon chips were added in the clay dispersion and ultrasonicated for 30 min. The physically mixed nylon clay chips were oven dried at 80° C. for 3 h and vacuum dried at 110° C. for 12 h. Nylon and nylon-clay nanocomposite master batches were spun on a laboratory scale DSM 5 Micro Twin Screw Compounder, Netherland, which was attached to a fibre winding device, under optimized spinning conditions, (i.e., temperature 240° C., screw speed at mixing 200 rpm, residence time 2 min and screw speed at spinning 100 rpm). The spinning was carried out under a nitrogen atmosphere.

The spun master batches were chopped into chips using a chopper machine. These chips were then used for the preparation of different nanocomposite fibers with varying clay concentrations on a DSM 5 Micro Twin Screw Compounder, Netherland, under optimized spinning conditions (i.e., temperature 240° C., screw speed at mixing 200 rpm, residence time 1 min, and screw speed at spinning 5 rpm). The antimicrobial clay concentration in the fibers/films can range from about 0.1 to about 10% by weight of the polymer nanocomposite and the drawn denier data for some of the compositions of different Nylon 6/Clay nanocomposite fibers is given in Table 7, below. The extruded fibers were drawn on a laboratory drawing machine with a two-stage drawing process at 70° C., and 120° C. respectively. All the fibers were fully drawn, i.e. to an extent beyond which the fibers turned white upon further drawing. The final denier of the fibers was in the range of 78-128. It will be appreciated, however, that fiber sizes need not be so limited, and that fibers in the range of from 0.1 to about 400 denier can be produced for a variety of purposes.

TABLE 7

Nylon 6/clay Nanocomposite Fiber Composition

| Fiber type | Clay concentration (% by weight of Nylon 6/ clay nanocomposite) | Drawn denier |
|---|---|---|
| Pristine Nylon 6 | 0.0 | 89 |
| Nylon 6/Na-MMT | 0.75 | 102 |
|  | 1.0 | 100 |
|  | 2.0 | 101 |
| Nylon 6/Ag-MMT | 0.75 | 107 |
|  | 1.0 | 115 |
|  | 2.0 | 114 |
| Nylon 6/Cu-MMT | 0.75 | 106 |
|  | 1.0 | 124 |
|  | 2.0 | 128 |
| Nylon 6/Cloisite-30B | 0.75 | 78 |
|  | 1.0 | 81 |
|  | 2.0 | 87 |
| Nylon 6/SA-MMT | 0.75 | 102 |
|  | 2.0 | 111 |
|  | 3.0 | 108 |

Preparation of Nylon 6/Clay Nanocomposite Films

Nylon 6/clay nanocomposite films were made using a compression moulding machine. Master batches having 10% (by weight) concentration of Ag-MMT (30° C. 7 Day), Cu-AM-MMT, Cloisite 30-B, Na-MMT and SA-MMT were used for making films. Films were made using following parameters:

Weight of master batch: 2 g
Temperature: 235° C.
Pressure: 10 Bars
Holding time: 2 Minutes Antimicrobial Activity of Nylon/Clay Nanocomposite Fibers The antimicrobial activity of fibers was determined quantitatively using AATCC-100-2004 against Gram positive bacteria *Staphylococcus aureus* and Gram negative bacteria *Escherichia coli*. The nylon and nylon/clay nanocomposite fibers (0.5 gm) were placed in 100 ml conical flask containing 20 ml Luria broth solution and sterilized. The flasks were inoculated with 10 μl of bacteria suspension ($10^6$ cfu/ml) and maintained for 24 h at 37° C. After incubation, bacterial colonies were counted on the surface of an agar plate. Serial dilutions of the bacterial suspensions were made in sterilized distilled water. Dilution of $10^{-4}$ and $10^{-5}$ were used for colony counting. 10 μl bacterial suspensions were spread on to the Luria agar plate, and the plates were incubated at 37° C. for 24 h. After incubation, bacterial colonies were counted. The test was carried out in duplicate and an average of two specimens was used in calculations. The neat nylon fibre sample was used as a control. The antimicrobial activity was calculated using following formula:

Antimicrobial activity (%)=$(A-B)/A \times 100$, where

A=Number of colony forming units (cfu/ml) in nylon fibre sample
B=No. of cfu/ml in nanocomposite fibre sample.

Washing of Nanocomposite Fibers

The antimicrobial activity of the nanocomposite fibers post-washing was evaluated. Washing of the fibers was carried out in a launder-o-meter at 50° C. for 45 min using Lissapol N as the non-ionic detergent per the ISO-2 test method.

Antimicrobial Activity of Nanocomposite Films

The qualitative disc diffusion test was used to evaluate the antimicrobial activity of the nanocomposite films. The nylon 6/clay nanocomposite films were cut into circular disc forms and sterilized. Each disc was placed on a bacteria-inoculated ($10^5$ cfu/ml) Luria agar plate. The plates were incubated at 37° C. for 24 h. The zone of inhibition was observed after a 24 h incubation period.

Metal Ion Elution

The release of copper and silver ions from nanocomposite fibers was tested in two simulated perspirations (acidic and alkaline) and in DI water (neutral pH). Acidic (pH 5.5) and alkaline (pH 8) simulated perspirations were prepared by the method described in the "Test method for color fastness to perspiration." See Nakashima, H.; Miyano, N.; Takatuka, T.; Journal of Health Science 54 (2008) 390. The simulated perspiration solutions acidic (pH 5.5) and alkaline (pH 8) were prepared by the method described in AATCC Test Method 15-2009, titled "Test method for color fastness to perspiration." For the preparation of acidic perspiration solution, L-histidine hydrochloride monohydrate (0.5 g), Sodium chloride (5 g) and disodium hydrogen phosphate (5 g) were dissolved in distilled water, mixed with NaOH 0.1 M to adjust the pH to 5.5. for the preparation of alkaline perspiration solution, L histidine hydrochloride monohydrate (0.5 g), NaCl (5 g) and disodium hydrogen phosphate were dissolved in pure water mixed with NaOH 0.1M to adjust the pH to 8.0. Elution experiments of metal ion release were performed using the following test procedure. Nanocomposite fiber (0.5 gm) containing 10% (by weight of the nanocomposite) antimicrobial clay was placed in a conical flask containing 60 ml solution of simulated perspiration and DI water. The conical flask was kept in an orbital shaker at 200 rpm for 8 days at 37° C. The liquid sample solutions were collected after the first and eighth days. The solutions were analysed by Inductive Coupled Plasma Mass Spectroscopy for silver and copper content.

Release of Drug from the Nanocomposite

The controlled drug release behavior of SA-MMT/Nylon 6 nanocomposite fibers was tested in phosphate buffered saline solution (pH 7.4). About 0.1 g of each fiber was taken and put in different conical flasks each containing 10 ml of saline buffer solution and kept in an incubation chamber at 37° C. with continuous stirring at 200 rpm. About 2 ml of the solution was taken out at regular time intervals and the corresponding absorbance value was measured in UV spectrophotometer at 259 nm, which is the characteristic peak of Sulphanilamide drug. The concentration of the drug was calculated using the standard characteristic curve obtained for Sulphanilamide at different concentrations.

Tensile Testing

Tensile testing of the clay loaded nanocomposite fibers was carried out on an Instron 4301 tester with a load cell of 1 kg (ASTM-D5035-90) and gauze length 50 mm. Fibers were tested for tensile properties like modulus, tenacity, and percentage elongation at break.

Results and Discussion

X-Ray Diffraction Analysis for Modified Clays

The average crystal structure of sodium montmorillonite, Cloisite 30B, silver and copper modified clays was analyzed by X-ray diffraction. FIG. 1 shows the X-ray diffractrogram of Sodium montmorillonite and Cloisite 30B. The X-ray diffractogram of Na-MMT showed the characteristic "d-spacing" of 12.49 Å at 2θ value of 7.12°. Small quantities of quartz, at 26.68° (2θ), and anorthite, at 20.07°, 26.71° and 28.63° (2θ), were also observed. Cloisite 30B clay has the bulky interlayer long tallow based chain alkyl ammonium ions, hence the (001) plane is shifted to the lower 2θ angle of 4.8° with high d-spacing of 18.08 Å. FIG. 1 illustrates that, in Cloisite 30 B the exchange of cations like Na+ by bulky quaternary ammonium ions has increased the interlayer d spacing of the MMT clay from 12.49 to 18.08 Angstrom.

Figure 2:
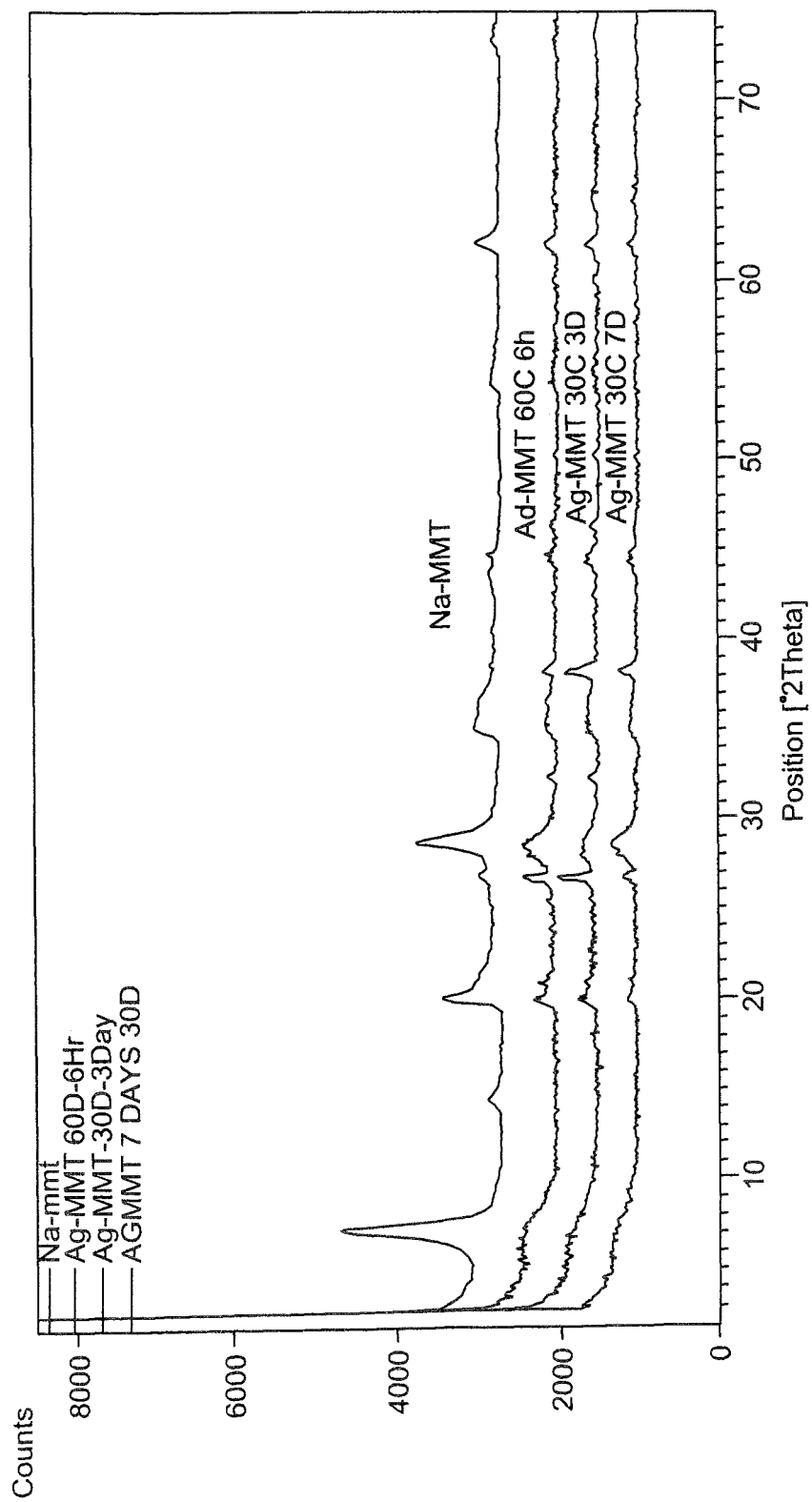
FIG. 2 illustrates the X-ray diffractrogram of silver modified montmomillonite clay.

FIG. 2 shows the X-ray diffractograms of silver modified montmorillonite clay. It has been observed that the peak of (011) plane became less intense and almost diffused with increase in reaction time. Similar results have been observed by Praus et al. when they studied the absorption of $Ag^+$ on sodium montmorillonite. See Praus, P., Turicova, M., Valaskova, M., J. Braz. Chem. Soc., 19 (2008) 549). With an increase in concentration of the silver nitrate solution, the content of $Ag^+$ in the MMT increased and the layered MMT structure gradually collapsed and exfoliated. In all experiments, a concentration of silver nitrate was used that was six times the cation exchange capacity (CEC) value of the clay.

Figure 3:
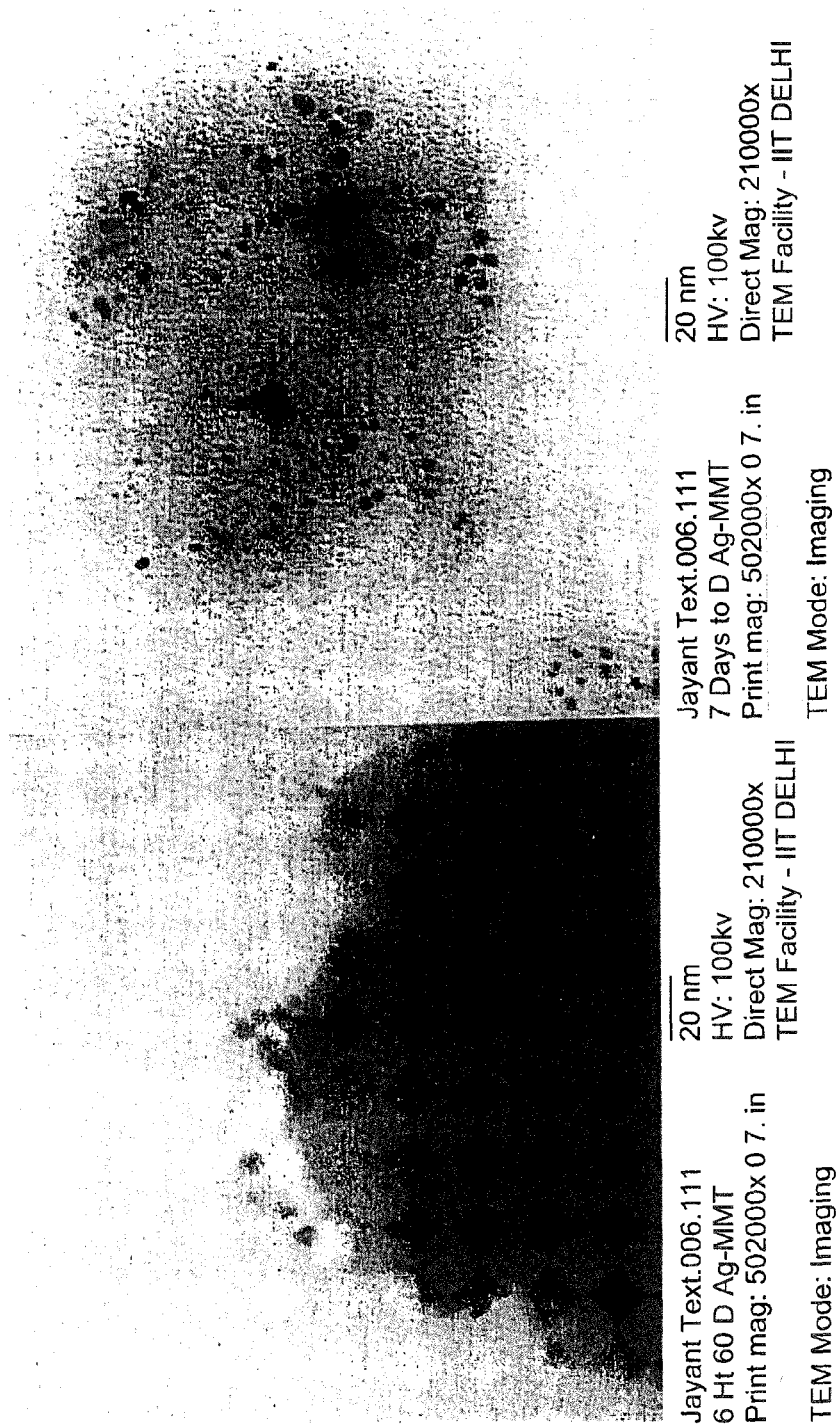
FIG. 3 illustrates the existence of very small silver nanoparticles (5-15 nm) on the surface of silver modified clay as observed under TEM.

The X-ray diffractrogram of silver modified clays also shows some small crystal peaks at 2θ value of 380, 440, 64° which corresponds to 111, 200 and 220 crystal faces of metallic silver. When the silver modified clay was observed under TEM, it was observed that there are silver very small nanoparticles (5-15 nm) on the surface of the clay (see FIG. 3). It has been reported in the literature that the addition of reducing agent in clay/silver nitrate suspension forms silver nanoparticles, and the clay acts as a stabilizer for the silver nanoparticles. See Su, H-L., Chou, C-C., Hung, D-J., Lin, S-H., Pao, I-C., Lin, J-H., Huang, F-L., Dong, R-X., Lin, J-J., Biomaterials, 2009. In this case, the inventors observed the presence of silver nanoparticles even without addition of any reducing agent.

Sodium montmorillonite clay has a large number of peripheral hydroxyl groups. In solution form these hydroxyl groups may act as mild reducing agent and lead to the formation of silver nanoparticles. The formation of the silver nanoparticles on the surface of the clay and in the intergallaries may be responsible for the complete exfoliation of the clay platelets.

Figure 4:
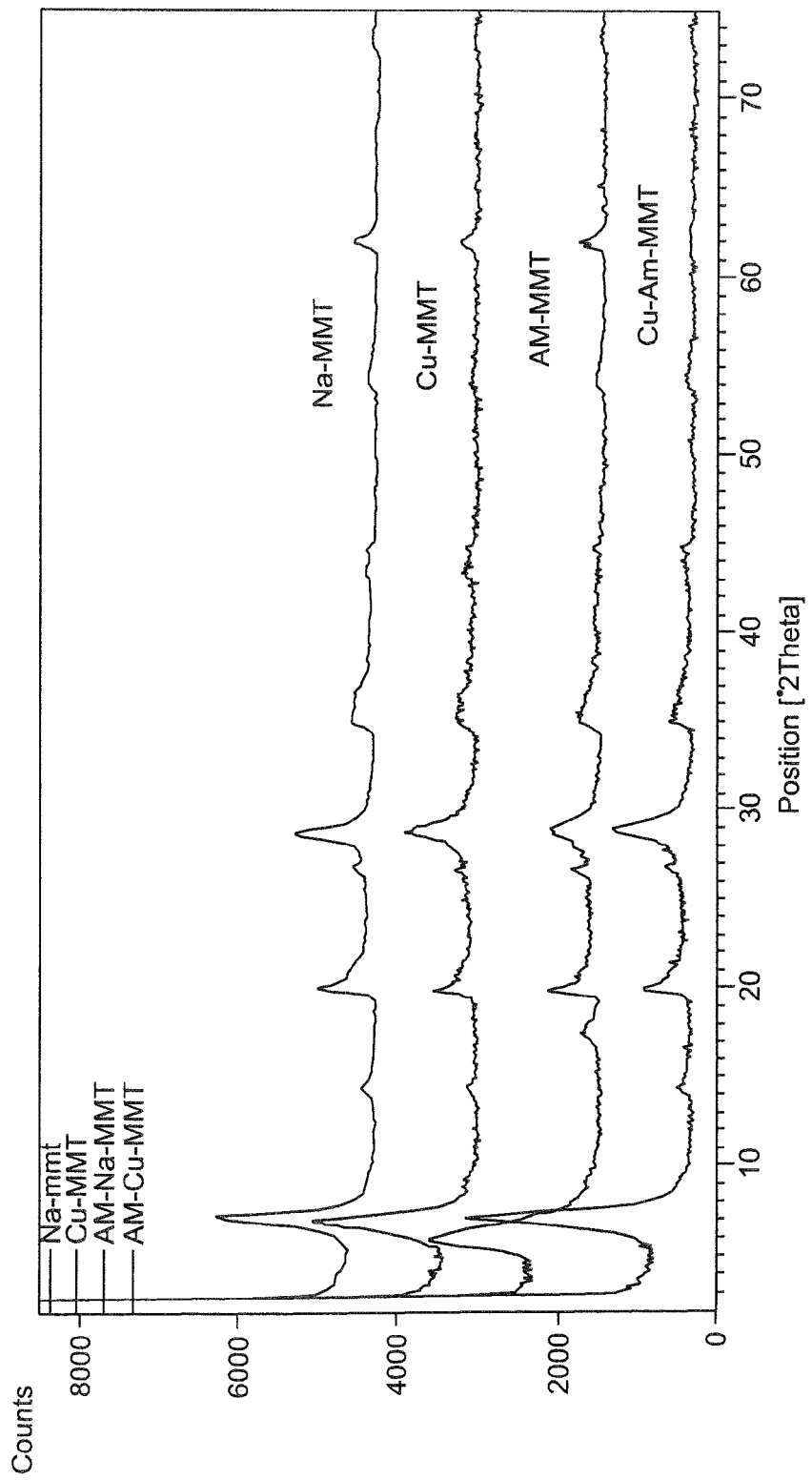
FIG. 4 illustrates X-ray diffractrogram of copper modified clays
Figure 5:
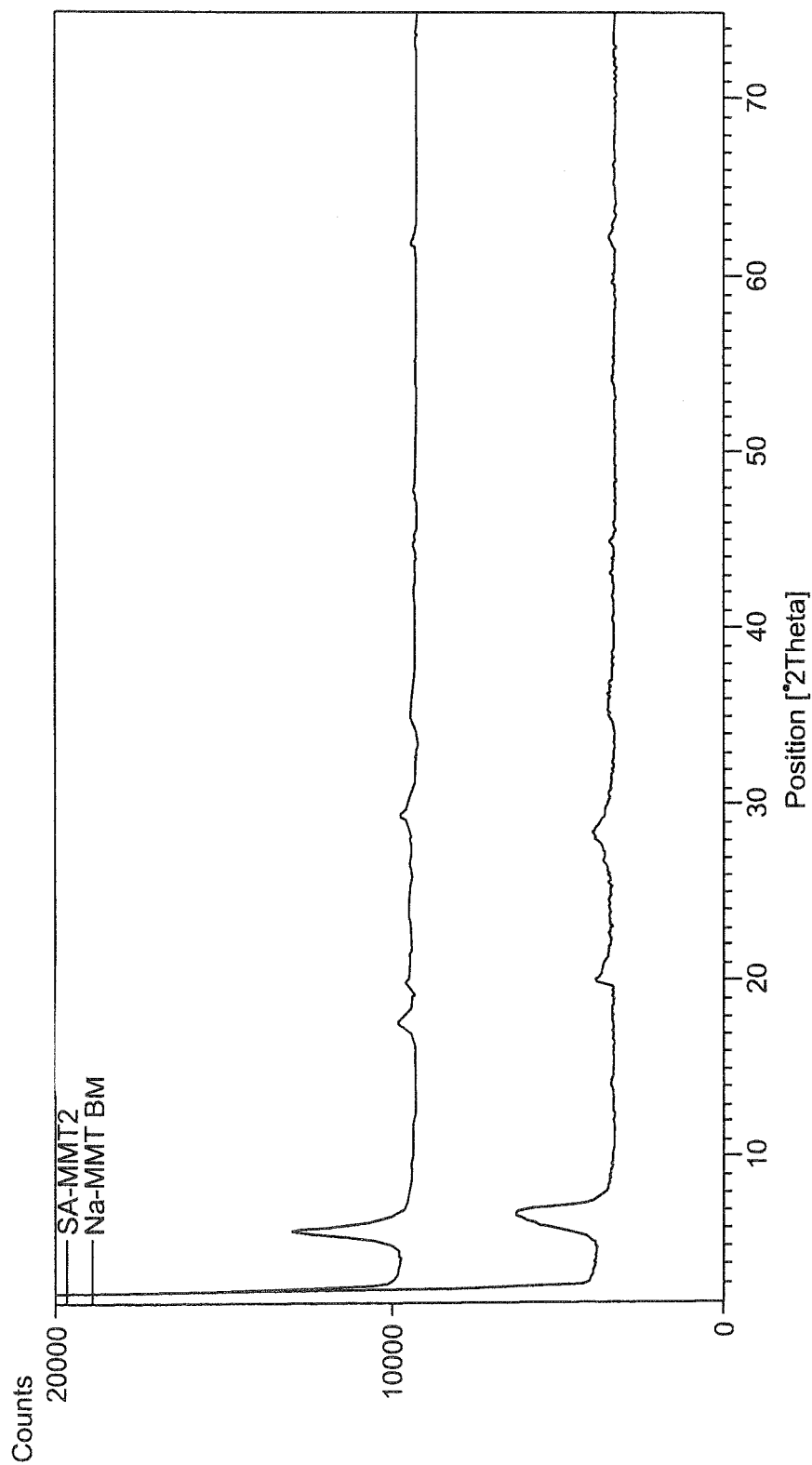
FIG. 5 illustrates X-ray diffractrogram of Sulphanilamide modified clay

The X-ray diffractograms of copper modified clays are shown in FIG. 4. It has been observed that after ion exchange with copper there is no change in the interlayer spacing. The interlayer spacing of copper modified clays is shown in Table 2, below. Hu and Xia, also reported no change in interlayer spacing of copper modified montmorillonite. However, the acid modified montmorillonite clays, which were ion exchanged with copper (Cu-AM-MMT), showed higher interlayer spacing in XRD, which proves that acid modification of Na-MMT clays helps in ion exchange with copper ions. Acid modified MMT has $H^+$ ions in the intergalleries as compared to $Na^+$, $K^+$ in Na-MMT. The $H^+$ ions are more easily replaced with $Cu^{++}$ as compared to $Na^+$, thus facilitating the loading of $Cu^{++}$ in MMT through ion exchange.

The montmorillonite clay has the layered structure and it is one dimension nanomaterial. The distance between the two layers of montmorillonite is also in the nano range. If these layers are stacked together, clay will not disperse into the polymer matrix at nano level and will not show the properties of nanocomposite. The addition of quaternary ammonium compound, silver, copper increases the interlayer d spacing of the montmorillonite clay due to exchange of smaller ions like Na+ by bigger ions like Ag+, Cu++ or the drug cation. Thus XRD results confirm that the MMT clay has been loaded with these ions as desired.

TABLE 2

Interlayer Spacing For The Modified Clays As Determined From XRD

| Clays | Interlayer Spacing (Å) | Angle (2θ) in ° |
|---|---|---|
| Na-MMT | 12.07 | 7.32 |
| Cu-MMT | 12.35 | 7.15 |
| AM-MMT | 14.80 | 5.96 |
| Cu-AM-MMT | 12.21 | 7.23 |
| SA-MMT | 14.80 | 5.97 |

Elemental Chemical Analysis for Clay by EDXS

Energy dispersive X ray analysis is used to analyze near surface elements and to estimate their proportions at different positions. Elemental chemical analysis of non-limiting examples of sodium montmorillonite, silver and copper modified clays was carried out and the results are summarized in Table 3, below. Na-MMT clay contains $Na^+$, $K^+$, $Ca^+$ ions, with the major ion being $Na^+$ accounting for about 2.01% of the clay weight. After the ion exchange reaction these interlayer cations are replaced by $Ag^+$ or $Cu^{++}$ ions. The highest loading of silver was 10.53% by weight of antimicrobial nanoclay found in Ag-MMT (30° C. 7 D) clay. The acid modified clay (Cu-AM-MMT) showed a higher amount of copper loading (8.5%) as compared to the unmodified clay (Cu-MMT). The silver or copper modified clay samples showed a decrement in $Na^+$, $K^+$ and $Ca^{++}$ content after ion exchange reaction. As a result, it can be said that these are the preferential exchangeable ions for $Ag^+$ or $Cu^{++}$. Magana et al. have prepared various silver loaded montmorillonite clays and the maximum amount of silver loading they have achieved is 8.37%, whereas with the clays prepared in the present disclosure, a higher loading of 10.53% has been achieved. Further optimization of the parameters of the ion-exchange process can achieve a quantity of antimicrobial agent (silver, copper, quaternary ammonium salt and the cationic drugs) in the clay that is about 1% to about 30% by weight of the antimicrobial nanoclay.

TABLE 3

Elemental Chemical Analysis Of Clays By Edx

| Elements | Si | Al | O | Mg | Fe | Mn | Na | K | Ca | Ag | C | N | Cu |
|---|---|---|---|---|---|---|---|---|---|---|---|---|---|
| Cloisite 30B | 18.72 | 9.37 | 53.91 | 1.42 | 2.65 | 0 | 0 | 0 | 0 | 0 | 5.7 | 7.92 | 0 |
| Na-MMT | 22.71 | 9.55 | 64.78 | 1.48 | 2.53 | 0.61 | 2.01 | 0.04 | 0.55 | 0 | 0 | 0 | 0 |
| Ag-MMT (60° C. 6 H) | 23.5 | 8.27 | 65.05 | 1.01 | 3.21 | 0.96 | 0 | 0 | 0.21 | 6.46 | 0 | 0 | 0 |
| Ag-MMT (30° C. 3 D) | 23.23 | 5.46 | 57.55 | 1.23 | 2.34 | 0.82 | 0 | 0 | 0.1 | 4.37 | 0 | 0 | 0 |
| Ag-MMT (30° C. 7 D) | 25.5 | 6.71 | 58.19 | 1.47 | 2.84 | 0.48 | 0 | 0 | 0.03 | 10.53 | 0 | 0 | 0 |
| Cu-MMT | 24.6 | 5.8 | 60.42 | 1.3 | 2.45 | 0.36 | 0 | 0 | 0 | 0 | 0 | 0 | 7.8 |
| Cu-AM-MMT | 25.8 | 10.4 | 63.4 | 2.1 | 1.5 | 0.61 | 0 | 0 | 0 | 0 | 0 | 0 | 8.5 |

Again silver loading in clay was confirmed by an ICP method and results are given in Table 4. The maximum silver loading of 4878 ppm was found in Ag-MMT (30° C. 7D) clay example. It has been found that in case of copper modified montmorillonite, the amount of copper ion loading is higher in acid modified montmorillonite (Cu-AM-MMT) example (24631 ppm) as compared to montmorillonite (Cu-MMT) example (16016 ppm).

TABLE 4

Analysis Of Silver And Copper Loading In Clays By ICP

| S. No. | Clays | Silver Loading (ppm) | Copper Loading (ppm) |
|---|---|---|---|
| 1 | Ag-MMT (60° C. 6 Hrs.) | 2867 | 0 |
| 2 | Ag-MMT (30° C. 3 Days) | 2768 | 0 |
| 3 | Ag-MMT (30° C. 7 Days) | 4878 | 0 |
| 4 | Cu-MMT | 0 | 16016 |
| 5 | Cu-AM-MMT | 0 | 24631 |

Evaluation of Antimicrobial Activity

Disc Diffusion Test for Clays

Figure 6:
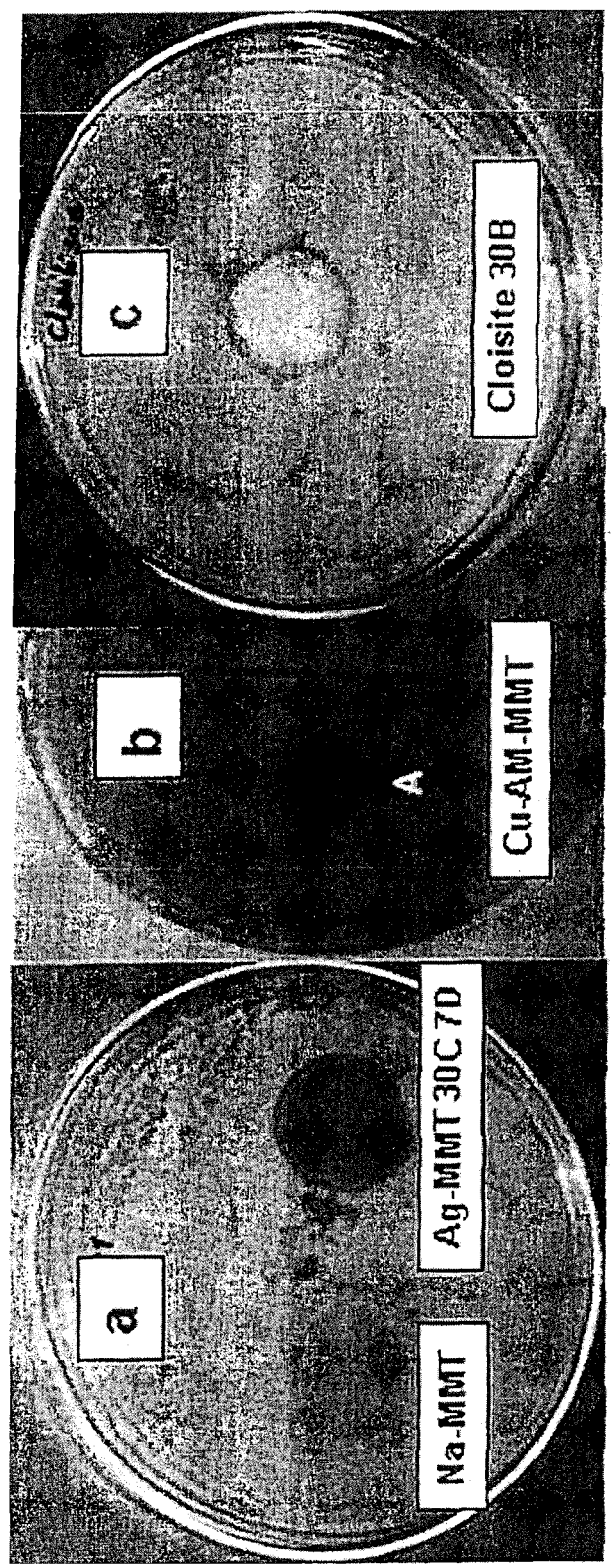
FIG. 6 shows antimicrobial activity of sodium montmorillonite, silver/copper modified clays tested against Gram positive bacteria *Staphylococcus aureus* and Gram negative bacteria *Escherichia coli* using qualitative disc diffusion test method.

The antimicrobial activity of the sodium montmorillonite, silver/copper modified clays was tested against Gram positive bacteria *Staphylococcus aureus* and Gram negative bacteria *Escherichia coli* using a qualitative disc diffusion test method as shown in FIG. 6. In the case of the unmodified montmorillonite clay filter disc, bacterial growth was observed. However, there is a clear zone of inhibition observed around the filter disc containing silver, copper and sulphanilamide modified clays. It shows that the silver, copper ions and drug release out from the modified clays and provide antimicrobial activity. The commercial clay (Cloisite 30B) also showed a clear zone of inhibition against both the bacteria. The zone of inhibition around all the samples was measured and summarized in Table 5, below.

TABLE 5

Zone Of Inhibition Determined Using Disc Diffusion Test For Modified Clays

| S No. | Clay | Initial Diameter (mm) | Final zone diameter (mm) | Zone of inhibition (mm) |
|---|---|---|---|---|
| 1 | Na-MMT | 15 | 15 | — |
| 2 | Cu-MMT | 15 | 40 | 25 |
| 3 | Cu-AM -MMT | 15 | 40 | 25 |
| 4 | Ag-MMT 30 C 3 D | 15 | 25 | 10 |
| 5 | Ag-MMT 30 C 7 D | 15 | 25 | 10 |
| 6 | Ag-MMT 60 C 6 h | 15 | 19 | 4 |
| 7 | Cloisite 30B | 15 | 19 | 4 |
| 8 | SA-MMT | 15 | 50 | 35 |

The minimum inhibitory concentration (MIC) of the modified clays was determined using a colony counting method. MIC is defined as the minimum concentration required for inhibiting the visible growth of the bacteria. The results are summarized in Table 6, below. The commercial clay Cloisite 30 B has the lowest MIC value of 25 ppm. In case of modified clays, Ag-MMT 30C7D and Cu-AM-MMT clays showed low MIC value of 400 ppm and 700 ppm respectively. The inventors have found a lower MIC value for the copper modified clays as compared to the MIC value (1000 ppm) reported earlier by Zhao et al., and Hu and Xia. This may be due to the higher loading of the copper content on the clay matrix in the modified clay samples of the present disclosure.

TABLE 6

Minimum Inhibitory Concentration (MIC) Of Clays

| | | Minimum inhibitory concentration (MIC) ppm | |
|---|---|---|---|
| S No. | Clays | *Escherichia coli* | *Staphylococcus aureus* |
| 1 | Ag-MMT (60 C 6 H) | 500 | 500 |
| 2 | Ag-MMT (30 C 3 D) | 1000 | 800 |
| 3 | Ag-MMT (30 C 7 D) | 400 | 400 |
| 4 | Cu-MMT | 1000 | 1000 |
| 5 | Cu-AM-MMT | 600 | 700 |
| 6 | Cloisite 30B | 25 | 25 |
| 7 | SA-MMT | — | 1500 |

Antimicrobial Activity Of Nanocomposite Fibers

The antimicrobial activity of the nanocomposite fibre was evaluated quantitatively using an AATCC 100 method against both Gram positive and Gram negative bacteria. The results are summarized in Table 8, below. As can be seen, the Na-MMT-nylon 6 nanocomposite shows very little activity against the Gram positive bacteria *Staphylococcus aureus*. This is believed to be due mainly to the absorption ability of the clay (i.e., the large surface area of the clay adsorbs the bacteria and prevents its reproduction to some extent).

TABLE 8

Antimicrobial Activity Of Nanocomposite Fibers

| | | Antimicrobial Activity (%) | |
|---|---|---|---|
| Sample Type | Clay Conc. | *Staphylococcus aureus* | *Escherichia coli* |
| Pristine Nylon 6 | 0.0 | — | |
| Na-MMT + Nylon 6 | 0.75 | 10 | 15 |
| | 1.0 | 13 | — |
| | 2.0 | 11 | — |
| | 3.0 | 15 | — |
| Ag-MMT + Nylon 6 | 0.75 | 49 | 45 |
| | 1.0 | 12 | — |
| | 2.0 | 15 | — |
| | 3.0 | 53 | — |
| Cu-AM-MMT + Nylon 6 | 0.75 | 100 | 75 |
| | 1.0 | 16 | — |
| | 2.0 | 27 | — |
| | 3.0 | 48 | — |
| Closite-30B + Nylon 6 | 0.75 | 100 | 100 |
| | 1.0 | 100 | — |
| | 2.0 | 100 | — |
| | 3.0 | 100 | — |

The Ag-MMT-nylon 6 nanocomposite fibre shows a moderate antimicrobial activity against *Staphylococcus aureus* under the test conditions. The antimicrobial activity of Ag-MMT-Nylon 6 composite fibre is believed to be due to both adsorption ability as well as the silver ion release which has additional bactericidal effect. Ag-MMT clay (0.75% by weight) loaded sample shows 49% antimicrobial activity against *Staphylococcus aureus*. It has been observed that with further increase in clay concentration up to 2% (by weight) clay loading, the antimicrobial activity of the Ag-MMT-nylon 6 nanocomposite fibre decreases.

The antimicrobial activity of the nanocomposite fibre is dependent on the availability of silver ions on the surface of the fibre and its diffusion from the fibre. The reduction of the activity may be due to agglomeration of the clay on the surface of the fibre. However, the Ag-MMT nylon 6 nanocomposite containing 3% (by weight) clay loading showed 53% antimicrobial activity against *Staphylococcus aureus*.

Similarly, in the case of the Cu-MMT nylon clay nanocomposite, with an increase in concentration of clay in nylon matrix from 0.75% to 2% (by weight), the antimicrobial activity decreases against gram positive bacteria. However, the 0.75% Cu-MMT clay loaded nanocomposite fibre shows 100% antimicrobial activity for gram positive bacteria. The antimicrobial activity of the nanocomposite fibre is also dependent on the availability of the copper ions on the surface of the fibre and their diffusion from the fibre surface. The reduction of the activity may be due to agglomeration of the clay on the surface of the fibre which reduces their surface availability for release of copper ions.

The nanocomposite fibers prepared using the commercial clay Cloisite 30B showed excellent antimicrobial activity against Gram positive and negative bacteria. The Cloisite 30 clay contains an alkyl chain with a quaternary ammonium ion in the interlayer gallery. In this case, the clay adsorbs the bacteria, and bactericidal effect is provided by the quaternary ammonium ion. The entire range of nanocomposite fibers containing 0.75% to 3% Cloisite 30B showed 100% activity. This may be because the compatibility of Cloisite 30B, an organo-modified clay with nylon matrix, is much better that Ag-MMT or Cu-MMT clays, which are more hydrophilic in nature.

Since all the nanocomposite samples containing 0.75% clay loading showed very good antimicrobial activity against Gram positive bacteria, these samples were tested against Gram negative bacteria *Escherichia coli* also. It was found that the antimicrobial activity of the nanocomposite fibre against Gram negative bacteria is similar to that of Gram positive bacteria.

Durability of Antimicrobial Activity to Washing

Durability of antimicrobial activity to washing was carried out for those samples that showed 100% antimicrobial activity against Gram positive bacteria (i.e. 0.75% Cu-MMT nylon 6 and 0.75% Cloisite 30B nylon 6 nanocomposite fibers). The antimicrobial activity was analyzed after first, fifth, tenth and fiftieth washes. The results are summarized in Table 9 below. It has been found that the nanocomposite fibers retain their antimicrobial activity even after the fiftieth wash. This shows that incorporation of Cu-MMT and Cloisite 30B clays in to nylon nanocomposite fibers leads to a durable antimicrobial activity against both Gram positive and Gram negative bacteria.

TABLE 9

Washing Durability Of Antimicrobial Activity For Composite Fibers

| Samples | Number of washes | Antimicrobial Activity (%) *Staphylococcus aureus* |
|---|---|---|
| 0.75% Cu-AM-MMT | 1 | 100 |
|  | 5 | 100 |
|  | 10 | 100 |
|  | 50 | 100 |
| 0.75% Cloisite 30B | 1 | 100 |
|  | 5 | 100 |
|  | 10 | 100 |
|  | 50 | 100 |

Antimicrobial Activity of Nanocomposite Films

Figure 8:
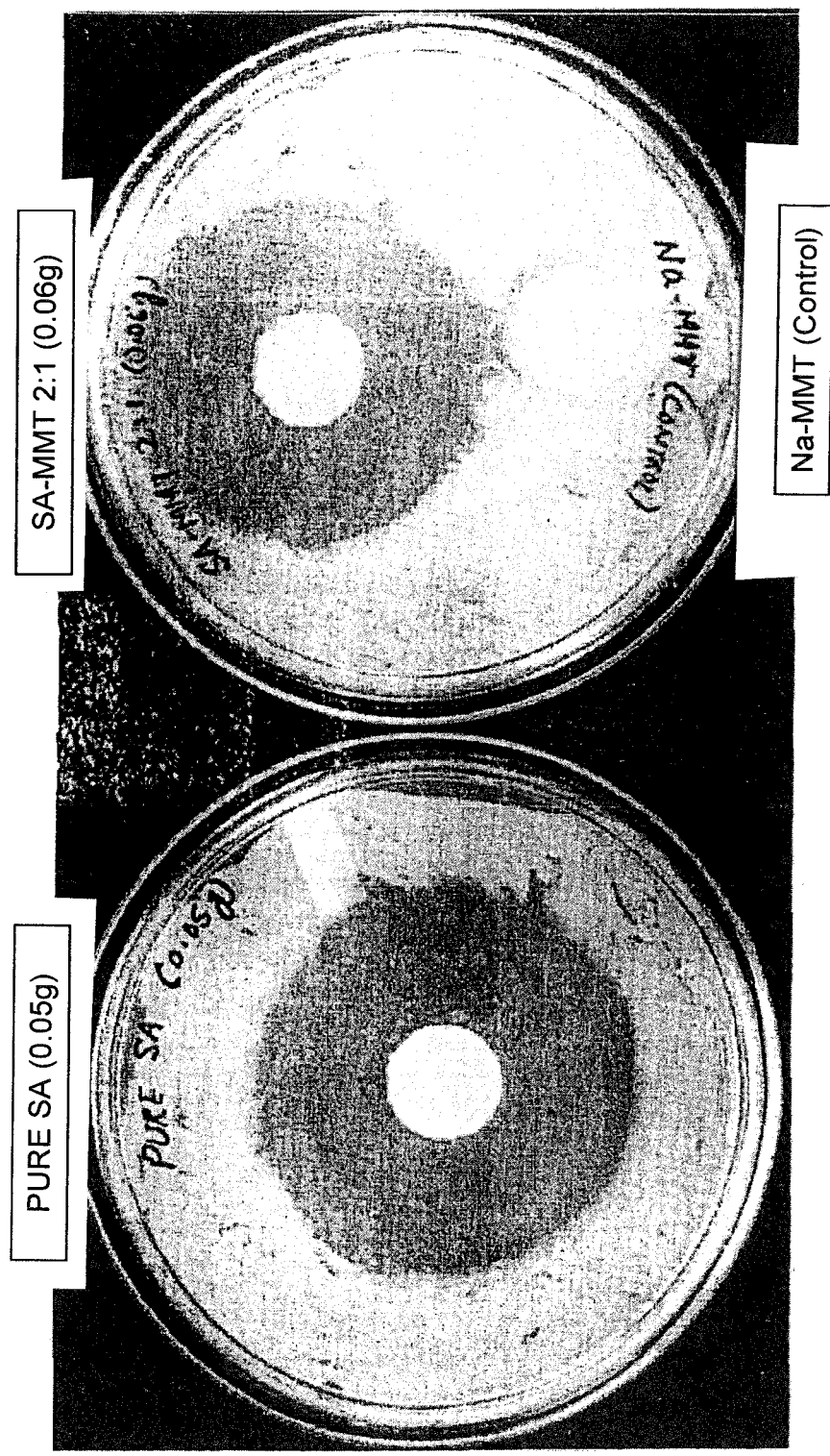
FIG. 8 illustrates zones of inhibition for nanocomposite films (a) 10% Na-MMT/Nylon 6 (b) 10% Cloisite 30B/Nylon 6 (c) 10% Cu-MMT/Nylon 6 (d) 10% Ag-MMT/Nylon 6 (all percentages are by weight of the polymer/clay nanocomposite)

The antimicrobial activity of the nanocomposite films was evaluated qualitatively using disc diffusion test method. The films were made with a high concentration (10% (by weight of the nanocomposite) of clay loading. At this concentration, all the films showed very good antimicrobial activity against Gram positive bacteria. The Cloisite 30B/Nylon 6 nanocomposite films created a small zone of inhibition, which shows that the Cloisite 30B leaches out from the film and creates a zone of inhibition. In the case of Ag-MMT/nylon 6 and Cu-MMT/nylon 6 nanocomposite films, there was no bacterial growth observed on the surface of the film. FIG. 8 shows the zones of inhibition for nanocomposite films: (a) 10% by weight of the nanocomposite Na-MMT/Nylon 6; (b) 10% Cloisite 30B/Nylon 6; (c) 10% Cu-MMT/Nylon 6; and (d) 10% Ag-MMT/Nylon 6.

Release of Copper and Silver from 10% Clay Loaded Nanocomposite

Figure 7:
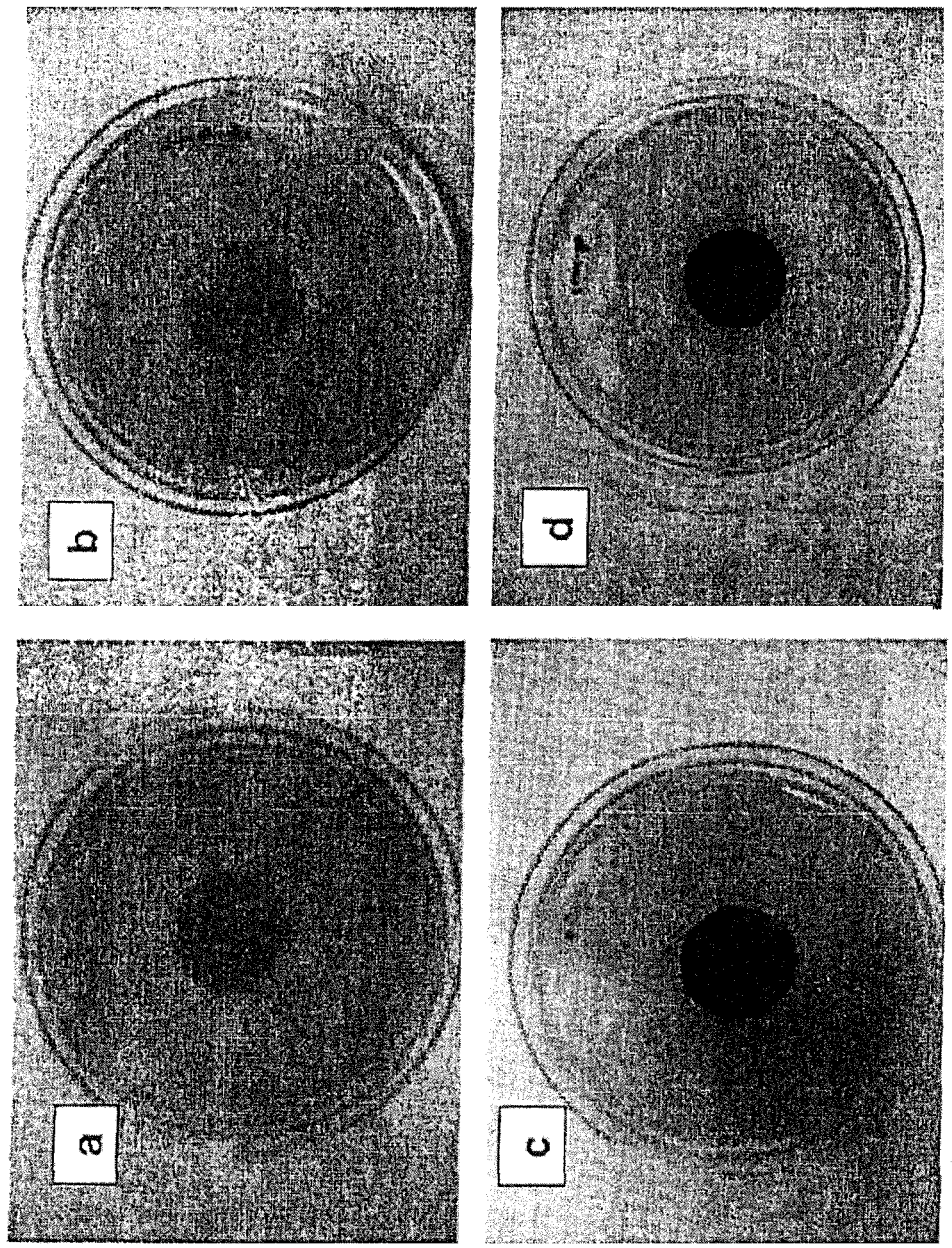
FIG. 7 shows antimicrobial activity of pure Sulphanilamide and Sulphanilamide modified clay tested against Gram positive bacteria *Staphylococcus aureus* using qualitative disc diffusion test method.
Figure 9:
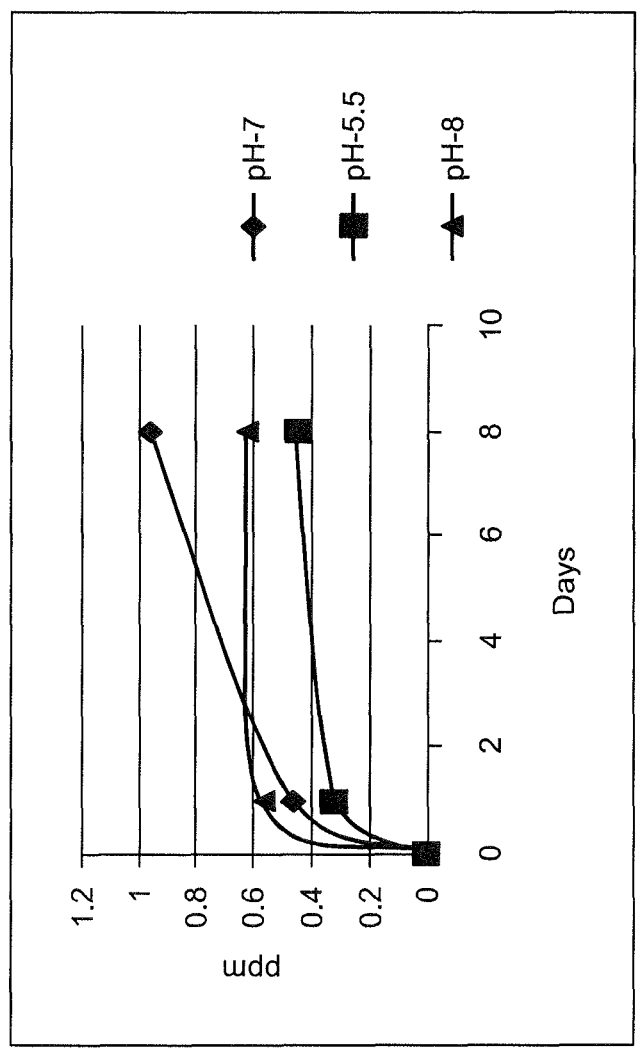
FIG. 9 is a graphical representation of a release profile of silver ions from nanocomposites.

To understand the mechanism of inhibition of bacteria by Ag-MMT-nylon 6 and Cu-MMT-nylon 6 nanocomposite, the release of silver and copper ion in different simulated perspiration solutions was assayed. It has been observed that the silver ions release faster in neutral and alkaline perspiration as compared to acidic perspiration (see FIG. 7). It is also observed that in case of acidic and alkaline condition, within two days, the entire silver ion releases from the nanocomposite. In the case of a neutral solution, the silver ion continuously releases from the nanocomposite. The amount of silver ion release within one day is 0.3-0.5 ppm. As noted, FIG. 9 shows the release profile of silver ions from nanocomposites.

Figure 10:
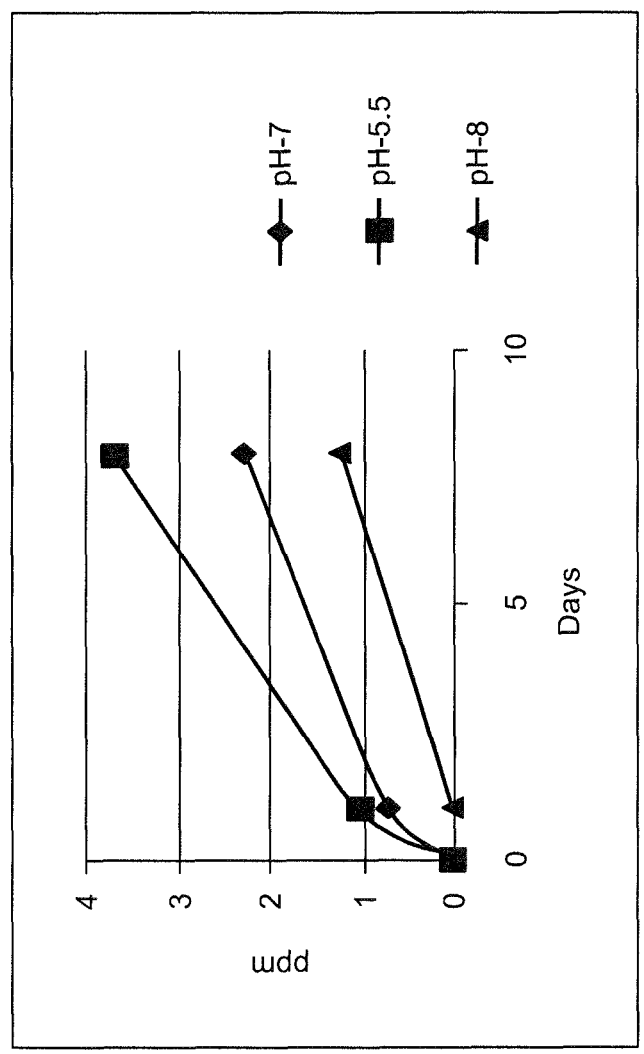
FIG. 10 is a graphical representation of a release profile of copper ions from nanocomposites.

The release profile of copper ions from Cu-MMT nylon 6 nanocomposites in different simulated perspiration solution is shown in FIG. 10. It has been observed that the copper ions continuously release from the nanocomposite fiber surfaces. The release of copper ions is faster in neutral and acidic perspiration as compared to alkaline perspiration. The amount of copper ion released within one day is 0.7-1.0 ppm in neutral and acidic simulated solutions.

It is, therefore, clear that copper ions released much faster than silver ions under the test conditions, which may be responsible for better activity of Cu-MMT based fibre over those based on Ag-MMT. In addition, it has also been observed in TEM and XRD studies that silver loading on clay is reduced to form silver nanoparticles of size 5-10 nm which are not seen in the case of Cu-MMT based clays.

Figure 11:
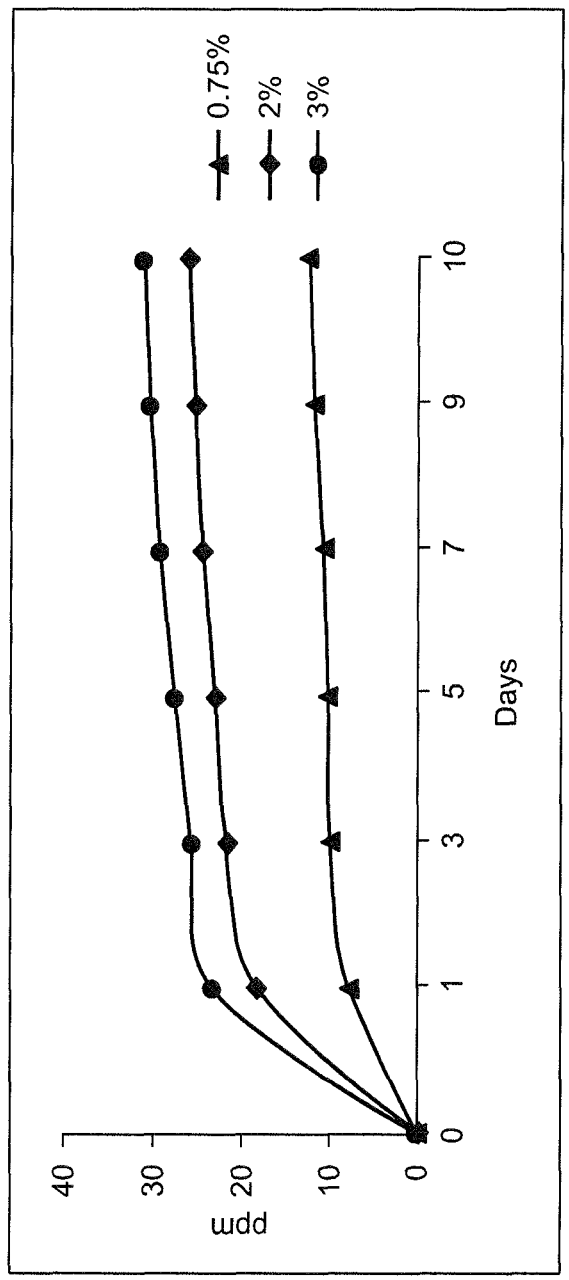
FIG. 11 is a graphical representation of release profile of Sulphanilamide from nanocomposite.

Release of Sulphanilamide from 0.75%, 2% & 3% SA-MMT Loaded Nanocomposite Fibers The release profile of drug from SA-MMT/nylon 6 nanocomposites in saline solution are shown in FIG. 11. It has been observed that the drug slowly releases from the nanocomposite fiber surfaces over a period of 10 days. The concentration of drug releases from the nanocomposite fibre increases with the clay loading.

Tensile Properties

Table 10 shows the mechanical properties for the nanocomposite fibers. For Na-MMT-Nylon 6 nanocomposite fibers, both strength and modulus fall with increasing clay loading.

TABLE 10

Mechanical Properties For The Nanocomposite Fibers

| Fiber Type | Clay Conc. (% by weight of Nylon 6/clay nanocomposite)) | Tenacity in grams per denier of fiber (gpd) | Coefficient of Variation (%) | Modulus (gpd) | Coefficient of Variation (%) | Elongation (%) (percentage change in length of the fiber at break during tensile testing) | Coefficient of Variation (%) |
|---|---|---|---|---|---|---|---|
| Neat nylon | 0 | 3.87 | 9.15 | 32.16 | 7.10 | 32.97 | 24.57 |
| Na-MMT | 0.75 | 3.82 | 4.65 | 32.05 | 5.62 | 33.61 | 26.62 |
|  | 1 | 3.51 | 6.51 | 30.62 | 8.21 | 34.58 | 7.27 |
|  | 2 | 3.50 | 5.40 | 30.35 | 9.39 | 32.20 | 8.85 |
|  | 3 | 3.20 | 6.42 | 29.67 | 10.96 | 30.66 | 10.60 |
| Cu-AM-MMT | 0.75 | 4.01 | 7.07 | 36.19 | 8.21 | 28.56 | 34.66 |
|  | 1 | 3.66 | 5.75 | 31.19 | 7.47 | 31.39 | 32.18 |
|  | 2 | 3.42 | 6.74 | 31.9 | 11.77 | 27.14 | 22.25 |
|  | 3 | 3.41 | 4.49 | 31.93 | 6.32 | 27.22 | 22.81 |
| Ag-MMT (30° C. 7 Days) | 0.75 | 3.82 | 4.45 | 32.02 | 6.69 | 30.83 | 33.21 |
|  | 1 | 3.58 | 6.14 | 31.92 | 6.02 | 29.67 | 22.78 |
|  | 2 | 3.51 | 7.11 | 31.61 | 7.06 | 29.39 | 18.03 |
|  | 3 | 3.46 | 5.29 | 30.16 | 7.83 | 30.31 | 17.32 |
| Cloisite 30B | 0.75 | 4.27 | 6.03 | 38.67 | 3.84 | 29.09 | 16.23 |
|  | 1 | 3.62 | 9.20 | 36.02 | 5.58 | 30.78 | 30.83 |
|  | 2 | 3.38 | 8.16 | 32.5 | 10.01 | 29.03 | 42.37 |
|  | 3 | 3.36 | 2.52 | 32.14 | 4.30 | 27.19 | 27.25 |
| SA-MMT | 0.75 | 4.12 | 4.82 | 33.07 | 7.24 | 27.54 | 17.43 |
|  | 2 | 3.52 | 6.52 | 31.15 | 6.24 | 30.20 | 28.23 |
|  | 3 | 3.28 | 6.90 | 31.42 | 6.50 | 29.58 | 26.35 |

Such decreases in strength and modulus may be due to agglomeration of Na-MMT clay which affects the polymeric chain orientation and hydrogen bonding. In the case of Cu-AM-MMT clay loaded nanocomposite fibers, the tenacity and modulus increases at 0.75% (by weight) clay loading, and then falls with further increases in loading. For Ag-MMT (30° C. 7 Day) clay loaded nanocomposite fibers, both strength and modulus fall with increased clay loading. For Cloisite 30B clay loaded nanocomposite fibers, initially, both strength and modulus increase up to 0.75% (by weight) clay loading, and then fall with further increases in clay loading. It is noted that for all the clays, the fall in tenacity and modulus is not very significant. Clay loading of 0.75% (by weight) leads to an enhancement of tensile strength by 4-11% and tensile modulus by 12-20% with a marginal decrease in elongation at break in all the three clays.

Figure 12:
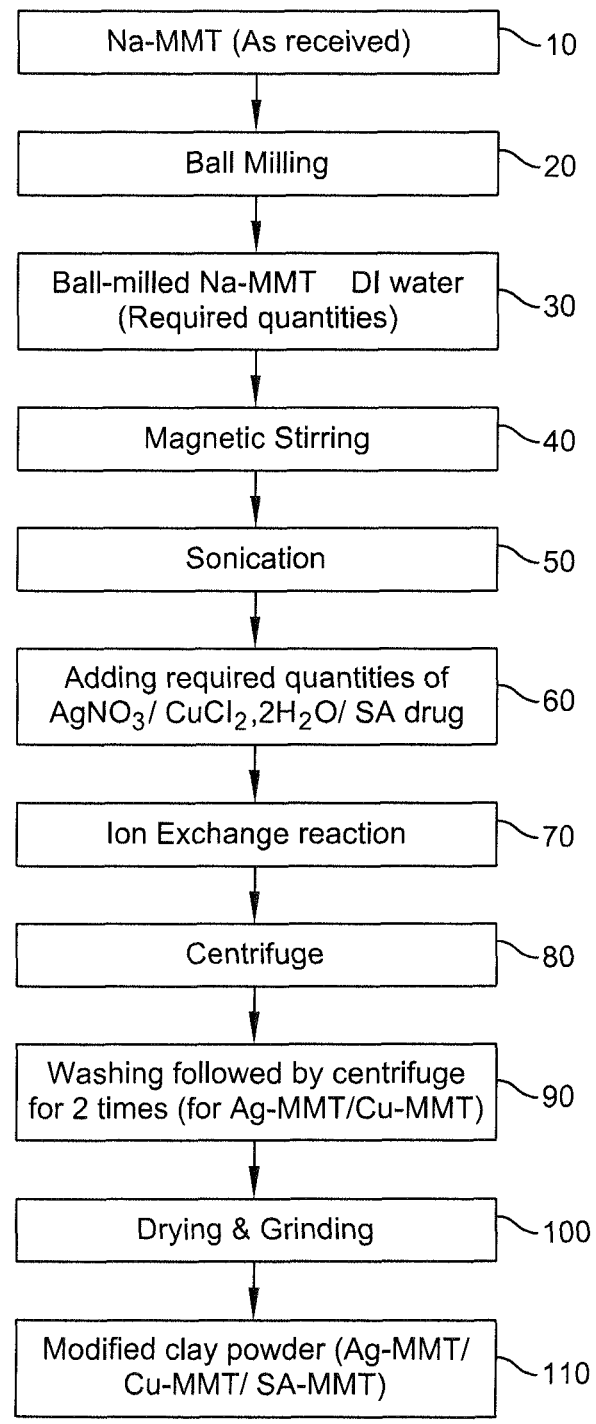
FIG. 12 is a flow chart describing an exemplary process for making a modified MMT clay.

Referring now to FIG. 12, an exemplary method will be described for making a modified MMT clay preparation (e.g., Ag-MMT/Cu-MMT/SA-MMT). At step 10, Na-MMT is provided. At step 20, the Na-MMT is subjected to ball milling. At step 30, the ball-milled Na-MMT is combined with deionized water. At step 40, the mixture is magnetically stirred, and at step 50 subjected to sonication. At step 60, appropriate quantities of $AgNO_3$, $CuCl_2.2H_2O$ and/or sulphanilamide drug, are added. The composition is subjected to an ion exchange reaction at step 70, followed by a centrifuging step (80). Two washing and centrifuging steps 90 are performed (for Ag-MMT or Cu-MMT clays), followed by a drying and grinding step 10 to obtain a quantity of modified clay powder (Ag-MMT, Cu-MMT or SA-MMT) at step 110.

Figure 13:
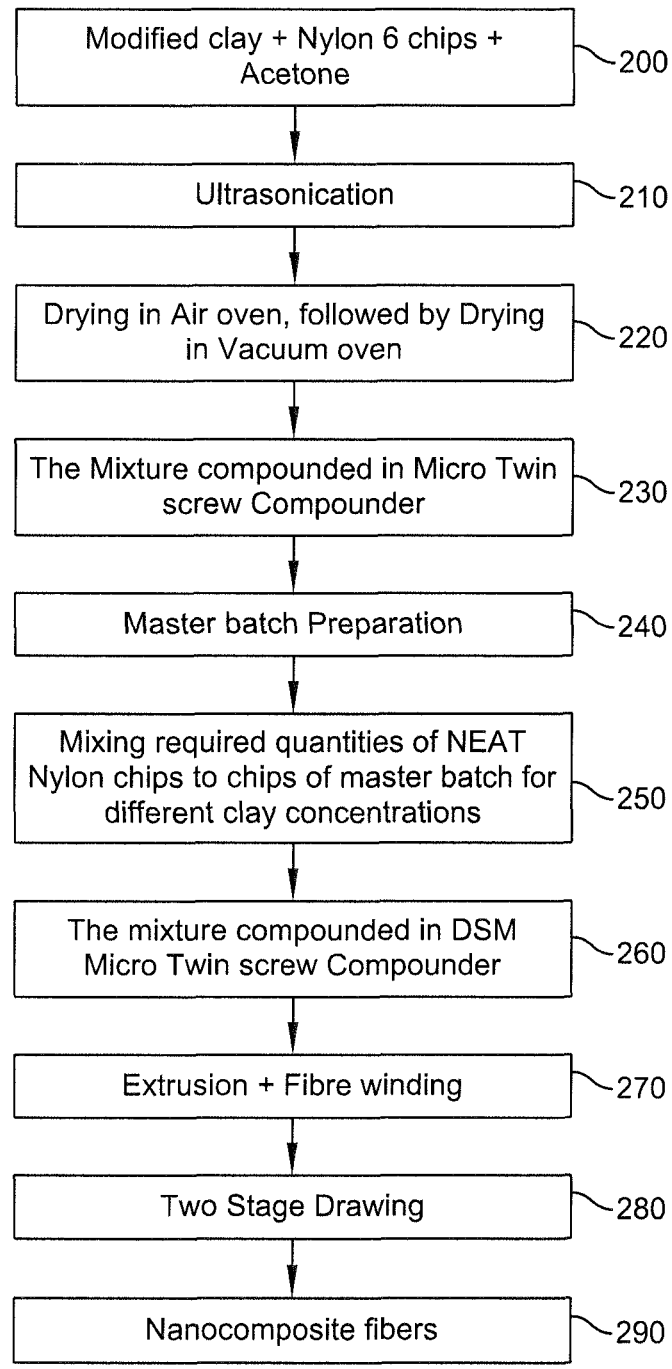
FIG. 13 is a flow chart describing an exemplary process for making nanocomposite fibers.

Referring to FIG. 13, an exemplary method will be described for preparing nanocomposite fibers. At step 200, a quantity of modified clay, Nylon 6 chips and acetone is provided. At step 210, the mixture is subjected to ultrasonication. At step 220, the ultrasonicated mixture is dried in an air oven, followed by drying in a vacuum oven. At step 230, the mixture is compounded in a micro twin-screw compounder. At step 240, a master batch is prepared. At step 250, appropriate quantities of neat Nylon chips are added to chips of the master batch to obtain a desired clay concentration. At step 260, the mixture is compounded in a DSM micro twin screw compounder. At step 270, the compounded material is extruded and fiber-wound. At step 280, a two stage drawing is performed, resulting in nanocomposite fibers at step 290.

CONCLUSION

Montmorillonite clay was modified with silver and copper metal ions by ion exchange reaction. The process conditions of varied to optimize for higher loadings of silver. The ion exchange reaction carried out at 30° C. for 7 days gave the highest silver loading (4878 ppm) on the clay. The formation of silver nanoparticles (5-15 nm) was observed on the surface of the all the silver modified montmorillonite clays as revealed by TEM and XRD studies. The silver modified clays showed an excellent antimicrobial activity against both Gram positive and Gram negative bacteria.

The unmodified (Na-MMT) montmorillonite and acid activated montmorillonite (AM-MMT) was used for copper ion exchange reaction. The acid activated copper montmorillonite (Cu-AM-MMT) showed a higher copper loading (24631 ppm) as compared to that of copper montmorillonite (Cu-MMT) (16016 ppm). The copper modified clays also showed a very good antimicrobial activity against both the tested bacteria. The antimicrobial activity of the commercial clay Cloisite 30B, which was modified with quaternary ammonium compound, was also tested. Cloisite 30B was shown to have a minimum inhibitory concentration value of 25 ppm which is very effective as compared to silver (MIC 400 ppm) and copper (MIC 700 ppm) modified clays. The higher activity of Cloisite 30B (lower MIC value) as compared to silver and copper modified clays may be due to much higher loading of organo cations in the Cloisite 30B clay.

It has been shown that nylon nanocomposite fibers developed using antimicrobial modified clays provide excellent antimicrobial properties. The modified clays were prepared using ion exchange methods to replace the cations (e.g., sodium, potassium) with antimicrobial metal ions such as silver, copper and quaternary ammonium. In addition, nylon nanocomposite fibers based on copper and quaternary ammonium ion modified clays show 100% antimicrobial activity against Gram positive *Staphylococcus aureus* and Gram negative *Escherichia coli* bacteria at an optimum clay loading of 0.75% (by weight). This activity is retained up to 50 washes.

A slow release of active agents is one advantage of these materials. Further, the addition of modified clays is found to enhance the tensile strength (4-11%) and tensile modulus (12-20%) of the nanocomposite fibers as compared to neat nylon fibers.

The addition of the quaternary ammonium modified clay has no effect on the color of the resulting filaments. The addition of copper and silver modified clay in filaments results in an off-white and pale golden yellow color, respectively. The addition of these modified clays in the filaments can improve the dye uptake of the filaments in subsequent dyeing operations. For example, polypropylene filaments can be dyed with different classes of disperse dyes in the presence of the clay. In one exemplary embodiment, polyurethane filaments can be dyed with acid dyes.

This disclosed process of imparting durable antimicrobial activity through modified clays can be applied to other fiber forming polymers such as polypropylene, polyester by melt spinning and acrylic or polyurethane fibers by solution spinning. The antimicrobial nanoclay material can be incorporated in the polymer matrix either by melt spun route for example in polypropylene, polyester, nylon or solution spun route for example in acrylic and polyurethane. However the process conditions for mixing and spinning of the fibers as well as the degree of dispersion of clay into the polymer would be different for different polymers listed here.

Similarly, it can also be used to make films and other molded forms from a range of polymers used in biomedical devices. In addition, the disclosed process can be extended to the incorporation of drug loaded clays for drug delivery applications, in the manner previously described.

Although the invention has been described in terms of exemplary embodiments, it is not limited thereto. Rather, the appended claims should be construed broadly to include other variants and embodiments of the invention, which may be made by those skilled in the art without departing from the scope and range of equivalents of the invention.

What is claimed is:

1. An antimicrobial textile composition having an intercalated and exfoliated morphology prepared by a process comprising the steps of:
    ball-milling an unmodified nanoclay untreated by modifiers, reducing agents, or antioxidants to generate a ball-milled nanoclay;
    ultrasonicating the ball-milled nanoclay to form a ball-milled and ultrasonicated nanoclay having an ion exchange capacity of 70-120 milliequivalents per 100 grams;
    incorporating into the ball-milled and ultrasonicated nanoclay via ion exchange a cationic antimicrobial agent selected from a group consisting of one or more of chlorhexidene acetate and sulphanilamide to form an antimicrobial nanoclay, wherein the cationic antimicrobial agent is 1% to 30% by weight of the ball-milled and ultrasonicated antimicrobial nanoclay; and
    twin-screw compounding a polymer selected from the group consisting of one or more of nylon, polypropylene, polyurethane, polyester, acrylic, and viscose into the antimicrobial nanoclay to form the antimicrobial textile composition having the intercalated and exfoliated morphology;
    wherein the combined quantity of the unmodified nanoclay and the cationic antimicrobial agent is 0.75% to 3% by weight of the composition; the composition achieves 100% antimicrobial activity against gram positive bacteria; and the composition retains a 100% antimicrobial activity against gram positive bacteria through 50 washings according to an ISO-2 test method.

2. The composition of claim 1, wherein the unmodified nanoclay serves as a carrier for the cationic antimicrobial agent.

3. The composition of claim 1, wherein the unmodified nanoclay is a montmorillonite clay having average particle size no larger than 500 nanometers.

4. The composition of claim 3, wherein the montmorillonite clay is selected from the group consisting of one or more of calcium montmorillonite, sodium montmorillonite, and acid-activated montmorillonite.

5. The composition of claim 1, wherein the antimicrobial nanoclay is incorporated into the polymer by a melt intercalation process or a solution intercalation process.

6. An antimicrobial fiber having an intercalated and exfoliated morphology, prepared by a process comprising the steps of:
    ball-milling an unmodified or acid-activated nanoclay untreated by modifiers, reducing agents, or antioxidants to generate a ball-milled nanoclay;
    ultrasonicating the ball-milled nanoclay to form a ball-milled and ultrasonicated nanoclay having an ion exchange capacity of 70-120 milliequivalents per 100 grams;
    incorporating into the ball-milled and ultrasonicated nanoclay via ion exchange a cationic antimicrobial agent selected from a group consisting of one or more of chlorhexidene acetate and sulphanilamide to form an antimicrobial nanoclay, wherein the cationic antimicrobial agent is 1% to 30% by weight of the ball-milled and ultrasonicated antimicrobial nanoclay; and
    twin-screw compounding a polymer selected from the group consisting of one or more of nylon, polypropylene, polyurethane, polyester, acrylic, and viscose into the antimicrobial nanoclay to form the antimicrobial fiber having the intercalated and exfoliated morphology;
    wherein the combined quantity of the unmodified or acid-activated nanoclay and the cationic antimicrobial agent is 0.75% to 3% by weight of the antimicrobial fiber; the antimicrobial fiber achieves 100% antimicrobial activity against gram positive bacteria; and the antimicrobial fiber retains a 100% antimicrobial activity against gram positive bacteria through 50 washings according to an ISO-2 test method.

7. The antimicrobial fiber of claim 6, wherein the fiber has a size of about 78-128 denier.

8. The antimicrobial fiber of claim 6, wherein the selected polymer is a nylon and the resulting antimicrobial fiber has a tensile strength that is 4-11% higher than a tensile strength of a similarly sized neat nylon fiber.

9. The antimicrobial fiber of claim 6, wherein the selected polymer is a nylon and the resulting antimicrobial fiber has a tensile modulus that is approximately 12-20% higher than a tensile modulus of a similarly sized neat nylon fiber.

10. The antimicrobial fiber of claim 6, wherein the nanoclay is a montmorillonite clay having average particle size no larger than 500 nanometers.

11. The antimicrobial fiber of claim 10, wherein the montmorillonite clay is selected from the group consisting of one or more of calcium montmorillonite, sodium montmorillonite, and acid activated montmorillonite.

12. An antimicrobial textile composition having an intercalated and exfoliated morphology prepared by a process comprising the steps of:

ball-milling an unmodified or acid-activated nanoclay untreated by modifiers, reducing agents, or antioxidants to generate a ball-milled nanoclay;

ultrasonicating the ball-milled nanoclay to form a ball-milled and ultrasonicated nanoclay having an ion exchange capacity of 70-120 milliequivalents per 100 grams;

incorporating into the ball-milled and ultrasonicated nanoclay via ion exchange a cationic antimicrobial agent selected from a group consisting of chlorhexidene acetate and sulphanilamide, and optionally one or more of silver ions, copper ions or quaternary ammonium ions, to form an antimicrobial nanoclay, wherein the cationic antimicrobial agent is 1% to 30% by weight of the ball-milled and ultrasonicated antimicrobial nanoclay; and twin-screw compounding a polymer selected from the group consisting of one or more of nylon, polypropylene, polyurethane, polyester, acrylic, and viscose into the antimicrobial nanoclay at a temperature of 240 degrees Celsius, with a residence time of between 1 and 2 minutes, and a mixing screw speed of 200 rpm, to form the antimicrobial textile composition having the intercalated and exfoliated morphology;

wherein the combined quantity of the unmodified or acid-activated nanoclay and the cationic antimicrobial agent is 0.75% to 3% by weight of the composition; the antimicrobial fiber achieves 100% antimicrobial activity against gram positive bacteria; and the antimicrobial fiber retains a 100% antimicrobial activity against gram positive bacteria through 50 washings according to an ISO-2 test method.

13. The composition of claim 12, wherein the unmodified or acid-activated nanoclay serves as a carrier for the cationic antimicrobial agent.

14. The composition of claim 12, wherein the unmodified or acid-activated nanoclay is a montmorillonite clay having average particle size no larger than 500 nanometers.

15. The composition of claim 14, wherein the montmorillonite clay is selected from the group consisting of one or more of calcium montmorillonite, sodium montmorillonite, and acid-activated montmorillonite.

16. The composition of claim 12, wherein the antimicrobial nanoclay is incorporated into the polymer by a melt intercalation process or a solution intercalation process.

* * * * *